(12) United States Patent
Tsao et al.

(10) Patent No.: US 8,871,156 B2
(45) Date of Patent: Oct. 28, 2014

(54) FLUID INTERFACE CARTRIDGE FOR A MICROFLUIDIC CHIP

(71) Applicant: Canon U.S. Life Sciences, Inc., Rockville, MD (US)

(72) Inventors: Ray Tsao, Germantown, MD (US); Hiroshi Inoue, Rockville, MD (US); Shulin Zeng, Gaithersburg, MD (US); Brian Murphy, Baltimore, MD (US); Kenton C. Hasson, Germantown, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 13/677,711

(22) Filed: Nov. 15, 2012

(65) Prior Publication Data

US 2013/0224845 A1 Aug. 29, 2013

Related U.S. Application Data

(62) Division of application No. 12/758,482, filed on Apr. 12, 2010, now Pat. No. 8,354,080.

(60) Provisional application No. 61/168,468, filed on Apr. 10, 2009.

(51) Int. Cl.
*G01N 15/06* (2006.01)
*G01N 33/00* (2006.01)
*G01N 33/48* (2006.01)
*B01L 3/00* (2006.01)
*G01N 35/10* (2006.01)
*B01L 9/00* (2006.01)

(52) U.S. Cl.
CPC ..... *B01L 3/502715* (2013.01); *B01L 2200/027* (2013.01); *B01L 2200/021* (2013.01); *B01L 2300/0816* (2013.01); *G01N 35/1095* (2013.01); *B01L 9/527* (2013.01); *G01N 2035/1034* (2013.01)

USPC .......... 422/503; 422/502; 422/509; 422/554; 422/560

(58) Field of Classification Search
CPC ....... G01N 15/06; G01N 33/00; G01N 33/48; G01N 15/14; G01N 15/1434; G01N 15/1463; G01N 15/147; G01N 15/1475; G01N 15/1484; B01L 3/5027; B01L 3/502707; B01L 3/502715; B01L 3/502776
USPC ............ 422/50, 68.1, 81, 502, 503, 509, 554, 422/560, 565, 566; 436/43, 174, 180
See application file for complete search history.

(56) References Cited

U.S. PATENT DOCUMENTS 5,188,148 A 2/1993 Garrison
6,103,199 A 8/2000 Bjornson et al.
(Continued)

FOREIGN PATENT DOCUMENTS

WO 96/04547 A 2/1996
WO 97/15394 A1 5/1997

OTHER PUBLICATIONS

Domansky et al., "Multiwell cell culture plate format with integrated microfluidic perfusion system," Proc. SPIE, vol. 6112, 61120F (2006) (abstract).
(Continued)

*Primary Examiner* — Brian J Sines
(74) *Attorney, Agent, or Firm* — Rothwell, Figg, Ernst & Manbeck, P.C.

(57) ABSTRACT

An interface cartridge for a microfluidic chip, with microfluidic process channels and fluidic connection holes at opposed ends of the process channels, provides ancillary fluid structure, including fluid flow channels and input and/or waste wells, which mix and/or convey reaction fluids to the fluidic connection holes and into the process channels of the microfluidic chip.

28 Claims, 21 Drawing Sheets

(56) References Cited

U.S. PATENT DOCUMENTS

| | | |
|---|---|---|
| 6,284,113 B1 | 9/2001 | Bjornson et al. |
| 6,306,659 B1 | 10/2001 | Parce et al. |
| 6,495,369 B1 | 12/2002 | Kercso et al. |
| 7,217,542 B2 | 5/2007 | Tyvoll et al. |
| 7,429,479 B2 | 9/2008 | Harding |
| 8,105,783 B2 | 1/2012 | Handique |
| 2002/0055167 A1 | 5/2002 | Pourahmadi et al. |
| 2002/0058329 A1 | 5/2002 | Singh et al. |
| 2004/0086424 A1 | 5/2004 | Schembri |
| 2005/0180894 A1 | 8/2005 | Petroff et al. |
| 2005/0249637 A1 | 11/2005 | Kawazoe et al. |
| 2005/0277125 A1 | 12/2005 | Benn et al. |
| 2006/0204403 A1 | 9/2006 | Federas |
| 2007/0111303 A1 | 5/2007 | Inoue et al. |
| 2007/0248976 A1 | 10/2007 | Harding |
| 2008/0003588 A1 | 1/2008 | Hasson et al. |
| 2008/0003594 A1 | 1/2008 | Hasson et al. |
| 2008/0056948 A1 | 3/2008 | Dale et al. |

OTHER PUBLICATIONS

Fontova et al., "Mulitple automated minibioreactor system for multifunctional screening in biotechnology," Conf. Proc. IEEE Eng. Med. Biol. Soc. 1:632-635 (2006) (abstract).

Rohde et al., "Microfluidic system for on-chip high-throughput whole-animal sorting and screening at subcellular resolution," PNAS 104(35:13891-13895 (2007) (abstract).

FLUID INTERFACE CARTRIDGE FOR A MICROFLUIDIC CHIP

PRIORITY CLAIM

This application is a divisional of and claims priority to U.S. patent application Ser. No. 12/758,482, filed on Apr. 12, 2010, which claims the benefit of provisional application Ser. No. 61/168,468, filed Apr. 10, 2009, each of which is incorporated herein by reference in their entirety.

BACKGROUND

1. Field of the Invention

The present invention relates to microfluidic devices and systems and, more specifically, to microfluidic devices and systems that include the use of external chips or cartridges that fluidically interface with microfluidic chips having one or more microfluidic channels.

2. Description of Related Art

Microfluidic chips are being developed for "lab-on-a-chip" devices to perform in-vitro diagnostic testing, including nucleic acid diagnostic assays, such as Polymerase Chain Reaction ("PCR"). The largest growth area for the use of such devices is in the field of molecular biology, where DNA amplification is performed in the sealed channels ("process channels") of the microfluidic chip. In one type of diagnostic assay that can be performed using such chips, optical detection devices are commonly used to measure the increasing amplicon product over time (Real Time PCR) and/or to perform a thermal melt to identify the presence of a specific genotype (High Resolution Thermal Melt). Exemplary disclosures related to the imaging of a microfluidic chip to measure the fluorescent product can be found in commonly-owned U.S. application Ser. No. 11/505,358 to Hasson et al. entitled "Real-Time PCR in Micro Channels" (U.S. Pat. Pub. 2008-0003588) and U.S. application Ser. No. 11/606,204 to Hasson et al. entitled "Systems and Methods for Monitoring the Amplification and Dissociation Behavior of DNA Molecules" (U.S. Pat. Pub. 2008-0003594), the respective disclosures of which are hereby incorporated by reference.

Conventional microfluidic chips comprise cartridges or cassettes with fluidic networking channels and sample/assay distribution wells formed therein. A typical microfluidic chip may comprise at least one or more microfluidic channels, fluidic connection holes, and reagent/waste wells. Microfluidic channel sizes are typically in the range of 10 to 300 μm, the sizes of fluidic connection holes are from 200 to 1500 μm, and the diameters of reagent/waste wells are typically in the range of 2000 to 5000 μm. Biological (chemical) reactions and assays take place within the microfluidic channels, or process channels, of the chip. A detection window may also be provided on the chip to enable detection of a characteristic of the reaction materials within the microfluidic channels, such as optical detection of reaction material colors. In addition, certain other process steps, such as thermal cycling and thermal melt, occur within the microfluidic process channels. To enable accurate optical detection and precision flow control, manufacturing tolerances of the process channels are quite stringent, and such chips are typically made of materials with superior optical qualities, such as glass, silica quartz, or high quality polymers.

Other functionality in the microfluidic chip includes the input, routing, mixing, and output of reaction materials (e.g., samples and reagents), which may be provided by flow structures that are ancillary to the process channels. Such ancillary fluid structures, (i.e., the "plumbing" of the chip) may be provided by various wells, such as a sample input well associated with each process channel, a waste well (pre and/or post process channel) associated with each process channel, and reagent input wells accessible to some or all process channels, and channels and connecting ports for mixing and routing the material to and from the process channels. Devices such as the Caliper sipper chip uses one or more sipper tubes attached to the microfluidic chip to access fluid samples and reagents held in a separate, free-standing microtiter plate. Such sipper tubes may be used as alternatives to or in combination with input wells formed in the chip itself.

In conventional microfluidic chips, the wells (input and/or waste wells) are connected directly to the fluidic holes coupling the process channels to the well(s). As a consequence, because the wells are much larger than the process channels, the chip capacity (i.e., the number of microfluidic process channels on the microfluidic chip) is limited by the size of the wells rather than that of the process channels. Moreover, channels in this portion of the microfluidic chip (i.e., the ancillary fluid structures) need not be as small and precisely manufactured as the process channels and there is no need for superior optic qualities in this part of the chip. Accordingly, the precision and material quality requirements in this part of the chip need not be as high as in the part of the chip containing the process channels.

FIGS. 1 and 2 depict a standard microfluidic chip assembly 10 having a microfluidic chip 18 having formed therein multiple microfluidic process channels 24 and fluidic connection holes 20, 22 on each end of each of the channels 24. Assuming a left-to-right flow direction through the process channels 24, fluidic connection hole 20 functions as an inlet port and fluidic connection hole 22 functions as an outlet port. Microfluidic chip 18 may be formed from multiple layers, such as upper layer 18a and lower layer 18b. As shown in FIG. 2, such a microfluidic chip 18 may be used with a secondary cartridge 12 that fits over top of the microfluidic chip 18, such that the fluidic connection holes 20, 22 of the microfluidic chip 18 line up directly with fluid input and/or waste collection wells 14, 16 of the secondary cartridge 12. Again, assuming a left-to-right flow direction, well 14 is a fluid input well for receiving fluid (e.g., sample, reagent, or a combination thereof) to be delivered to the inlet port 20, and well 16 is a waste collection well for receiving fluid from the outlet port 22. In this manner, the user can supply quantities of materials to the reagent wells which can then be drawn into the microfluidic chip via methods known in the art such as vacuum pressure, positive pressure, electrokinetics, capillary action and the like. Similarly, materials that have traversed the microfluidic channels can be drawn into the waste wells via the same methods.

Assembly 10 is limited by the size of the microfluidic chip 18 and the spacing of the process channels 24 on the chip in order to allow the direct placement of the wells 14, 16 present on the secondary cartridge 12 directly over the fluidic connection holes 20, 22, respectively, of the microfluidic chip 18. That is, the number and size of wells 14, 16 are constrained by the need to correspond directly to the fluidic connection holes 20, 22 and the process channels 24 of the microfluidic chip 18.

There are several challenges that exist in connection with the development of in-vitro diagnostic microfluidic chips including how to perform multiple sample tests simultaneously and how to access a large number of reagents, primers and assays efficiently to screen for desired tests. Current high throughput systems are located in hospital and clinical laboratories. These systems are often very large (with robotic system, pumps, tubes, and reservoirs) and very expensive to operate in point-of-care testing facilities. The desired goal is to develop an efficient assay delivery system for performing multiple sample tests on a desktop system.

Thus, there exists a desire for methods and apparatus to provide larger volume reagent and waste wells to microfluidic chips, specifically in a manner that allows for an increase in the number of microfluidic channels that can be placed on a chip without being confined by the size of necessary reagent/waste wells.

Accordingly, cost savings and other efficiencies can be achieved by minimizing the size of the microfluidic chip formed from costly materials and requiring precise manufacturing, while providing adequate ancillary fluid structures for mixing and/or routing reaction materials to the process channels without increasing the size and complexity of the microfluidic chip.

SUMMARY

Aspects of the invention are embodied in an interface cartridge providing a fluid flow network for delivering fluid to inlet ports of a microfluidic assay chip having a plurality of microfluidic channels, each microfluidic channel having an inlet port for delivering fluid to a proximal end of the microfluidic channel and an outlet port for removing fluid from a terminal end of the microfluidic channel. The interface cartridge includes a cartridge body having formed therein a plurality of fluid delivery channels in fluid-communication with a one or more microfluidic channels in the microfluidic assay chip. The cartridge body further includes a delivery interface configured to fluidly couple the fluid delivery channels of the interface cartridge to the microfluidic assay chip. The delivery interface includes a plurality of fluid delivery ports, and each fluid delivery port is associated with one fluid delivery channel and is configured to deliver fluid from the fluid delivery channel to an inlet port of one of the microfluidic channels. Each fluid delivery channel comprises a primary fluid channel having a proximal end and a terminal end, a vent well at the terminal end of the primary fluid channel, and a secondary fluid flow channel extending from a portion of the primary fluid channel between the proximal and terminal ends and terminating at one of the fluid delivery ports of the delivery interface.

According to further aspects of the invention, the interface cartridge further includes a fluid inlet well at the proximal end of each fluid delivery channel.

According to further aspects of the invention, the interface cartridge further includes a plurality of fluid removal channels corresponding in number to the number of microfluidic channels in the microfluidic assay chip and a waste interface configured to fluidly couple the fluid removal channels to the microfluidic assay chip. The waste interface includes a plurality of fluid transfer ports corresponding in number to the number of microfluidic channels in the microfluidic assay chip, and each fluid transfer port is associated with one fluid removal channel and is configured to receive fluid from an associated outlet port of one of the microfluidic channels. The interface cartridge may include waste collection wells disposed at a terminal end of each fluid removal channel.

According to further aspects of the invention, the path of each fluid delivery channel is configured so that the lengths of all fluid delivery channels are the same.

According to further aspects of the invention, the path of each fluid removal channel is configured so that the lengths of all fluid removal channels are the same.

According to further aspects of the invention, the plurality of fluid delivery channels corresponds in number to the number of microfluidic channels in the microfluidic assay chip.

According to further aspects of the invention, the interface cartridge further includes a sample port formed in the cartridge body and associated with each fluid delivery channel, each sample port being in fluid-communication with its associated fluid delivery channel and being configured for introducing a sample fluid into the associated fluid delivery channel.

According to further aspects of the invention, the interface cartridge further includes a common reagent port formed in the cartridge body to be in fluid-communication with all the fluid delivery channels and configured to introduce a reagent fluid into all the fluid delivery channels.

According to further aspects of the invention, the interface cartridge further includes a sipper tube extending from the cartridge body so that a distal end thereof can be placed into a reagent reservoir so that reagent can be drawn from the reservoir and into the sipper. The sipper is in fluid-communication with all the fluid delivery channels so that a reagent fluid drawn into the sipper can be introduced into all the fluid delivery channels.

According to further aspects of the invention, the interface cartridge further includes one or more sipper tubes extending from the cartridge body so that a distal end thereof can be placed into a sample reservoir so that a sample can be drawn from the reservoir and into the sipper. The sipper is in fluid-communication with the sample port so that a sample drawn into the sipper can be introduced into the associated fluid delivery channel.

According to further aspects of the invention, the cartridge body is made from a polymer, such as a transparent polymer or polymethyl methacrylate (PMMA). The cartridge body may be made from two or more layers.

According to further aspects of the invention, the interface cartridge further includes a gasket at the delivery interface and/or the waste interface disposed between the cartridge body and the microfluidic assay chip.

According to further aspects of the invention, the interface cartridge further includes a sample input well disposed at a proximal end of each of the fluid delivery channels and a plurality of reagent input wells, each of the reagent input wells being in communication with each of the fluid delivery channels.

According to further aspects of the invention, the interface cartridge further comprises a plurality of h-channels fluidly connecting each of the reagent input wells to each of the fluid delivery channels.

According to further aspects of the invention, the interface cartridge is configured to correspond to a standard 96-well plate and comprises eight sample input wells, eight vent wells, and eighty reagent input wells.

According to further aspects of the invention, the cartridge body has a rectangular shape and comprises a rectangular opening formed therein and wherein the delivery interface is disposed on one side of the rectangular opening and the waste interface is disposed on an opposite side of the rectangular opening.

According to further aspects of the invention, the interface cartridge further comprises an angled slot formed along one edge of the rectangular opening.

According to further aspects of the invention, the fluid delivery channel further comprises a sample flow region, a reagent flow region and a mixing region configured to permit mixing of the sample and the reagent, the mixing region being located at an intersection of the sample flow region and the reagent flow region.

Aspects of the invention are also embodied in an microfluidic assembly including a microfluidic assay chip and an interface cartridge. The microfluidic assay chip has a plurality of microfluidic channels, each microfluidic channel having an inlet port for delivering fluid to a proximal end of the microfluidic channel and an outlet port for removing fluid from a terminal end of the microfluidic channel. The interface cartridge is larger in width and length than the microfluidic assay chip and has formed therein a plurality of fluid delivery channels in fluid-communication with one or more microfluidic channels in the microfluidic assay chip. Each of the fluid delivery channels has a fluid delivery port configured to deliver fluid from the associated fluid delivery channel to an inlet port of one of the microfluidic channels.

In accordance with certain embodiments of the microfluidic assembly each fluid delivery channel of the interface cartridge comprises a primary fluid flow channel having a first leg and a second leg, each leg having a proximal end and a terminal end, and a vent well at the terminal end of the second leg of the primary fluid flow channel. The microfluidic assay chip comprises two inlet ports, one of the inlet ports being in fluid-communication with the terminal end of the first leg of the primary fluid flow channel and the other of the inlet ports being in fluid-communication with the proximal end of the second leg of said primary fluid flow channel. The microfluidic assay chip also includes a secondary fluid flow channel connecting the two inlet ports and including a portion extending toward at least one of the microfluidic channels of the microfluidic assay chip.

The microfluidic assay chip may be made from glass or silica quartz, and the interface cartridge may be made from plastic. The microfluidic assay chip may comprise a PCR region and a thermal melt region.

Aspects of the invention are embodied in an apparatus to increase chip capacity in a microfluidic chip. The apparatus comprises a primary microfluidic chip with at least one microfluidic channel and associated connection holes and a secondary cartridge comprising reagent/waste wells, connection holes, and fluidic extension channels. The reagent/waste wells of the secondary cartridge are connected to the at least one microfluidic channel and associated connection holes of the primary microfluidic chip via the connection holes and fluidic extension channels of the secondary cartridge.

In accordance with other aspects of the invention, random access is provided between reagent wells and sample channels in the secondary cartridge.

Further aspects of the invention are embodied in a microfluidic assembly comprising a microfluidic assay chip and an interface cartridge. The microfluidic assay chip comprises a plurality of microfluidic channels, two inlet ports associated with each of said microfluidic channels, an outlet port for removing fluid from a terminal end of the microfluidic channel. Each pair of inlet ports associated with each microfluidic channel is connected by an interconnecting channel that is in fluid-communication with a proximal end of the associated microfluidic channel. The interface cartridge comprises a plurality of fluid delivery channels in fluid-communication with the interconnecting channel of each of one or more microfluidic channels in the microfluidic assay chip. The interface cartridge further includes a delivery interface configured to fluidly couple the fluid delivery channels of the interface cartridge to the microfluidic assay chip. The delivery interface includes a plurality of fluid delivery ports, and each fluid delivery port is associated with one fluid delivery channel and is configured to deliver fluid from the fluid delivery channel to an interconnecting channel of the one or more microfluidic channels.

The above and other aspects and embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

The present invention provides secondary, interface cartridges or chips, referred to herein as interface cartridges, which enable the use of greater numbers or quantities of reagents, samples, and other materials without being limited by the configuration or space available on a traditional microfluidic chip.

Figure 1:
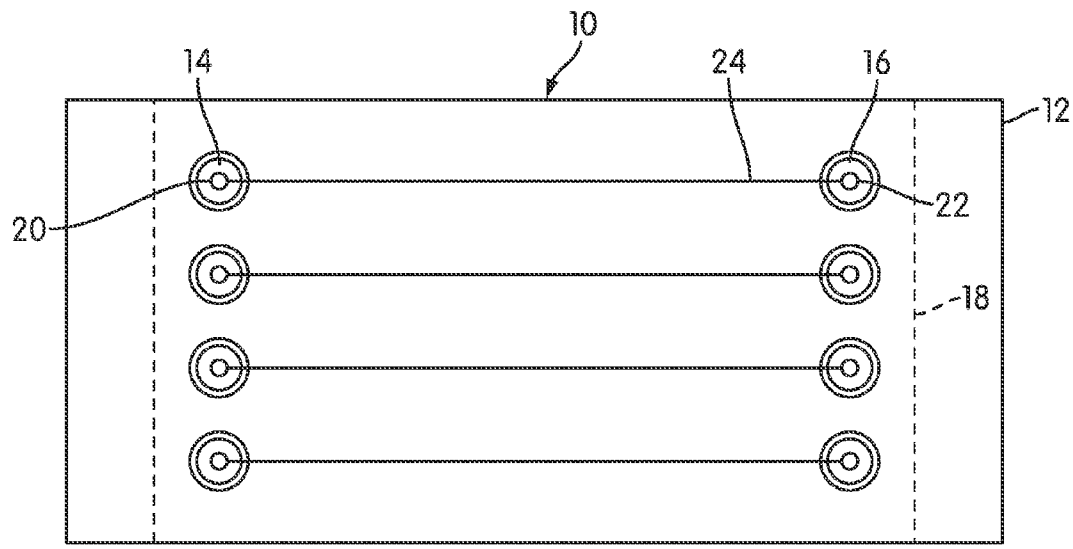
FIG. 1 is a top plan view of a conventional microfluidic chip having four process channels, four input wells, and four waste wells.
Figure 2:
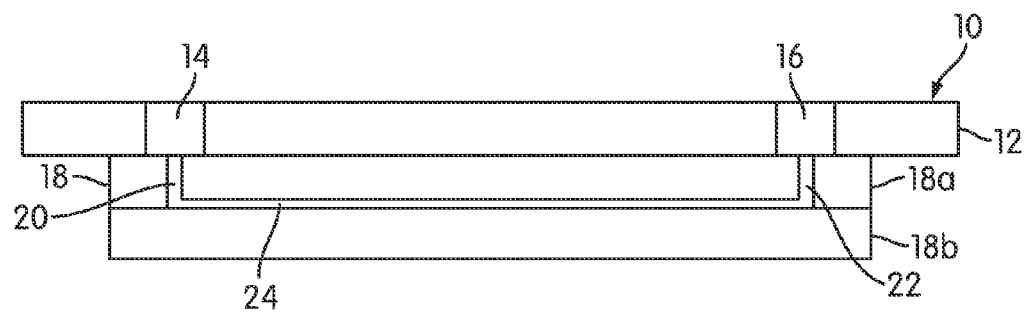
FIG. 2 is a side view of the conventional microfluidic chip.
Figure 3:
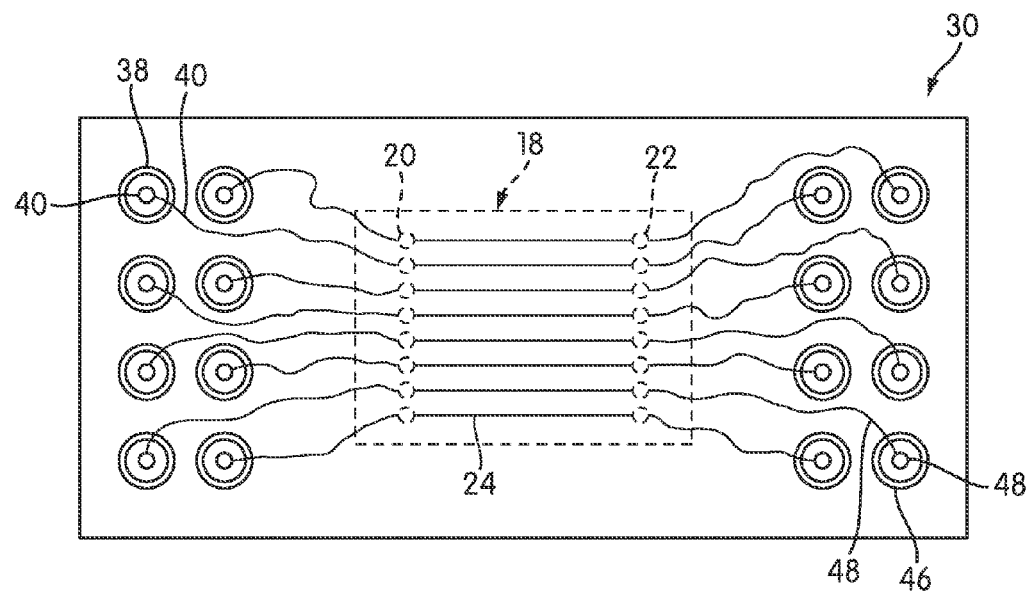
FIG. 3 is a top plan view of an interface cartridge and a microfluidic chip (shown in hidden line in FIG. 3) in which the process channels are provided in the microfluidic chip, and the ancillary fluid structures are provided in the interface cartridge.
Figure 4:
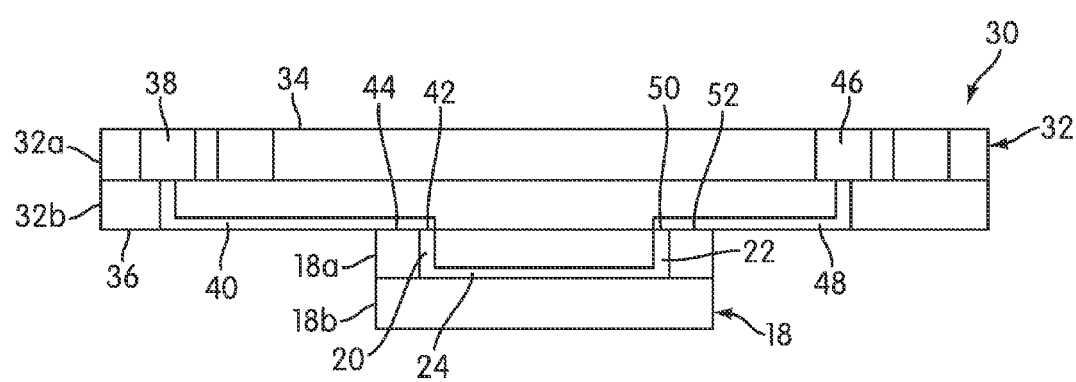
FIG. 4 is a side view of the interface cartridge/microfluidic chip arrangement of FIG. 3.

An assembly of an interface cartridge and a microfluidic chip embodying aspects of the present invention is designated generally by reference number 30 in FIGS. 3-4. Assembly 30 includes a microfluidic chip 18 coupled to an interface cartridge 32 embodying aspects of the present invention. Microfluidic chip 18 may be formed of, for example, glass, silica, or quartz, and may include an upper layer 18a and a lower layer 18b. Microfluidic chip 18 further includes microfluidic process channels 24 with an inlet port 20 and outlet port 22 disposed on opposite ends of each microfluidic process channel. A portion of each microfluidic chip 24 may comprise a thermal melt region in which thermal melt analysis is performed and a portion may comprise a PCR region at which PCR temperature cycling is performed. Interface cartridge 32 includes a cartridge body formed of a top layer 32a and a lower layer 32b and defining a top side 34 and a bottom side 36. A plurality of input wells 38 are formed in the top side 34 of the interface cartridge 32, and, in one embodiment each well 38 is in fluid-communication with one associated microfluidic process channel 24 via a fluid delivery channel 40. Each input well 38 is configured to receive a sample, reagent, or combination thereof. A portion of the contents of the well 38 is drawn into the associated microfluidic process channel 24 via fluid delivery channel 40 by methods known in the art such as vacuum pressure, positive pressure, electrokinetics, capillary action and the like.

In the illustrated embodiment, the number of input wells 38 (eight) and fluid delivery channels 40 corresponds to the number of microfluidic process channels 24, although configurations in which the numbers of input wells, fluid delivery channels, and microfluidic process channels differ are contemplated.

The inlet ports 20 of the microfluidic process channels 24 are fluidly coupled to the fluid delivery channels 40 at a delivery interface 44 at which a fluid delivery port 42, which comprises the terminal end of each fluid delivery channel 40, is coupled in fluid-communication with the inlet port 20 of the associated microfluidic process channel 24. An interface gasket, described in more detail below, may be provided between the interface cartridge 32 and the microfluidic chip 18 at the delivery interface 44.

A plurality of waste collection wells 46 are formed in the top side 34 of the interface cartridge 32, and each well 46 is in fluid-communication with one associated microfluidic process channel 24 via a fluid removal channel 48. Each waste collection well 46 is configured to collect materials from the microfluidic process channels 24 at the conclusion of the assay. Materials may be drawn from the microfluidic process channels 24 into the wells 46 via fluid removal channels 48 by methods known in the art such as vacuum pressure, positive pressure, electrokinetics, capillary action and the like.

In the illustrated embodiment, the number of waste collection wells 38 (eight) and fluid removal channels 48 corresponds to the number of microfluidic process channels 24, although configurations in which the numbers of waste collection wells, fluid removal channels, and microfluidic process channels are greater or less than eight are contemplated, as are configurations where there are unequal numbers of waste collection wells, fluid removal channels, and microfluidic process channels.

The outlet ports 22 of the microfluidic process channels 24 are fluidly coupled to the fluid removal channels 48 at a waste interface 52 at which a fluid removal port 50, which comprises the terminal end of each fluid removal channel 48, is coupled in fluid-communication with the outlet port 22 of the associated microfluidic process channel 24. An interface gasket may be provided between the interface cartridge 32 and the microfluidic chip 18 at the waste interface 52.

The assembly 30, and in particular the interface cartridge 32, as shown in FIGS. 3 and 4, eliminate the constraints found in the art by providing a larger interface cartridge which allows for the use of multiple input and/or waste wells which can vary in size. Rather than requiring that the input and/or waste collection wells be placed over the fluidic connection holes 20, 22 of the microfluidic chip 18, the input/waste collection wells 38, 46 are connected to the fluidic connection holes 20, 22 of the microfluidic chip 18 by fluid delivery/removal channels 40, 48 within the interface cartridge 32. This allows the placement of a greater number of wells of varying sizes.

A chip interface concept has been devised that utilizes a common 96-well plate format for assay reagent input. An assembly incorporating such a concept and embodying aspects of the present invention is represented by reference number 60 in FIGS. 5-12. The assembly 60 includes an interface cartridge 62 and a microfluidic chip 18. The format has been specially designed with microfluidic control, mixing, and delivery functions such that random access assays can be delivered to the microfluidic process channels of a PCR and thermal melting microfluidic chip.

Figure 5:
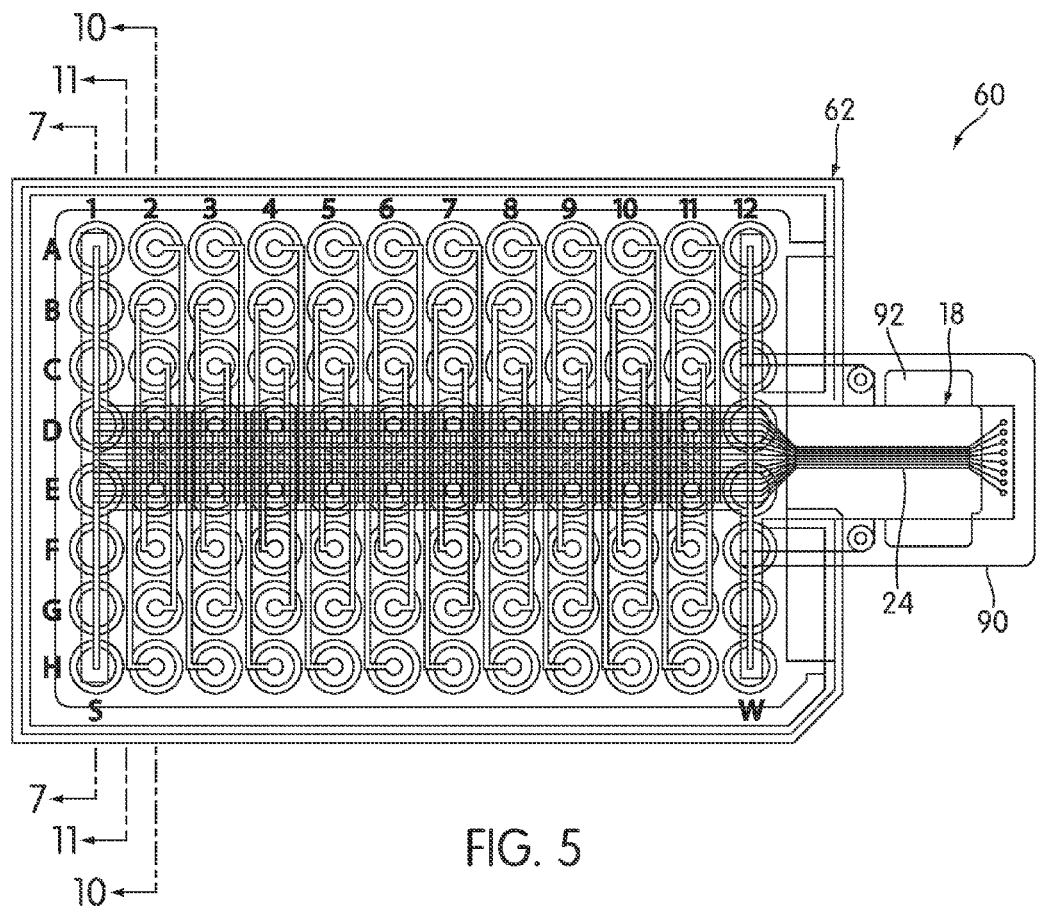
FIG. 5 is a top plan view of an interface cartridge having 96 wells for sample input, reagent input, and waste output coupled to a microfluidic chip with eight process channels, wherein each of the sample input wells and each of the waste output wells is fluidly coupled to one associated process channel and each of the reagent input wells is fluidly coupled to all of the process channels.
Figure 6:
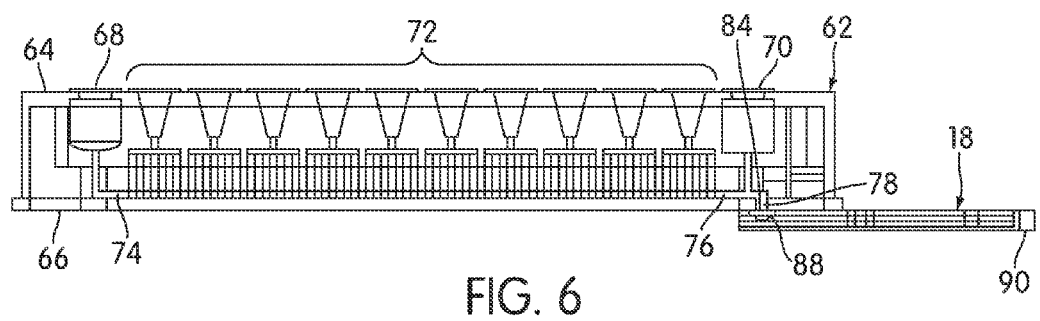
FIG. 6 is a side view of the interface cartridge/microfluidic chip arrangement shown in FIG. 5.
Figure 7:
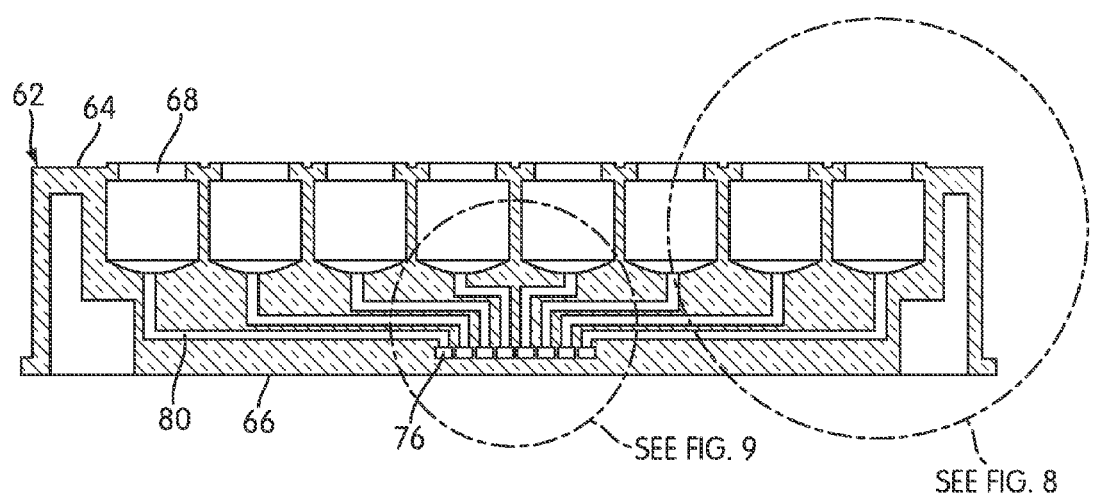
FIG. 7 is a cross-sectional view of the interface cartridge of FIG. 5, taken along the line 7-7.
Figure 8:
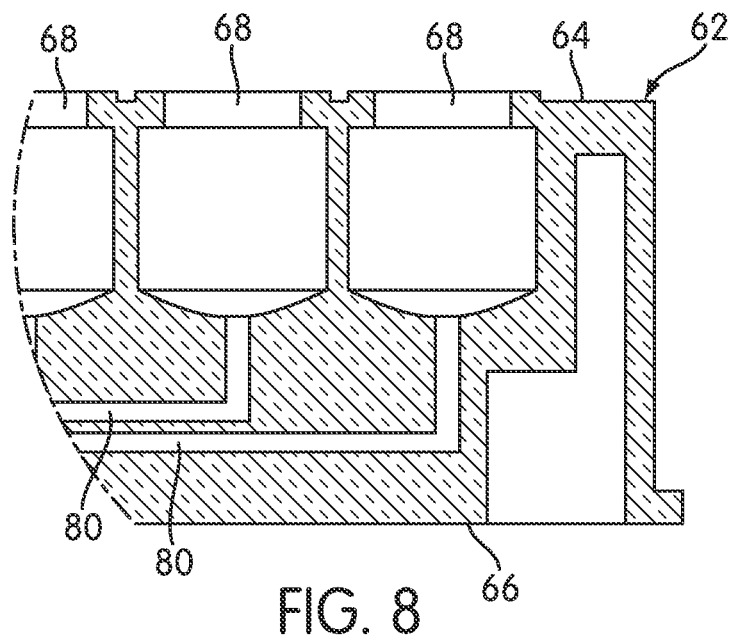
FIG. 8 is a detail of a portion of the cross sectional view of FIG. 7.
Figure 9:
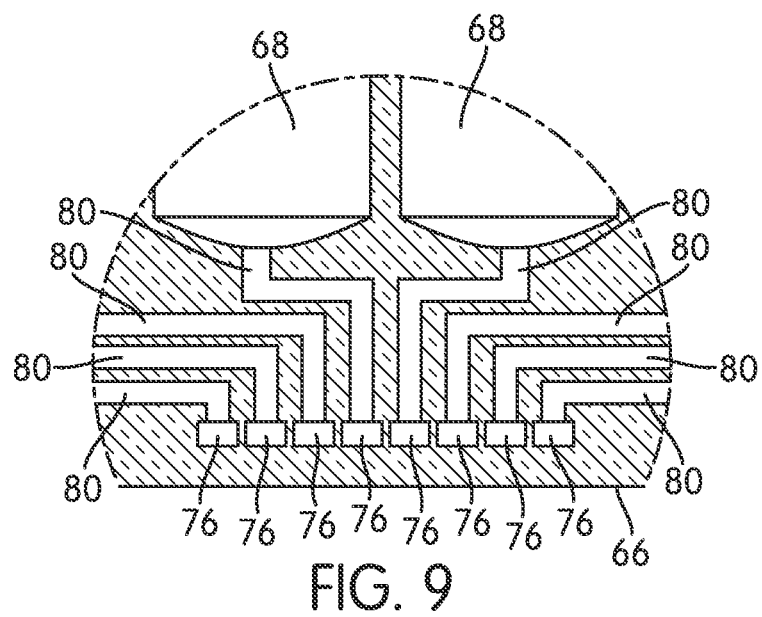
FIG. 9 is a detail of a portion of the cross sectional view of FIG. 7.

FIGS. 5 and 6 depict a 96-well interface cartridge 62 as one embodiment of the present invention, with a microfluidic chip 18, delivery interface 86 and a connection gasket 88 between the interface cartridge 62 and the microfluidic chip 18. The layout of the wells can be seen from the top view of the interface cartridge 62, FIG. 5. In one embodiment, the 96 wells are divided into 12 rows (numbered 1-12) of eight wells (lettered A-H). Row 1 comprises sample wells 68, rows 2 to 11 comprise primer/reagent wells 72, and row 12 comprises vent wells 70. In one embodiment, with the illustrated 96-well design, eight samples carried in the sample wells 68 can be tested simultaneously with each sample having random access to the eighty reagents/primers contained in any of the reagent wells 72. This concept is not limited to the eight sample wells and the eighty reagent/primer wells. Additional samples and additional reagents/primers can be implemented with a larger or reconfigured well plate design, both of which are contemplated within the scope of the present invention.

The flow pattern in the 96-well interface cartridge can be seen from the side view in FIG. 6. Fluid delivery channels 74 connect the sample wells 68, reagent wells 72, vent wells 70, and fluid delivery ports 84 at which fluid is delivered to each microfluidic process channel of the microfluidic chip 18. More specifically, the fluid delivery channels 74 include a primary fluid channel 76 associated with each sample well 68 for conveying sample material from the associated sample well 68 toward the associated vent well 70. The fluid delivery channels 74 further include sample delivery channels 80 (see FIG. 7) connecting each sample well 68 with its associated primary fluid channel 76, reagent delivery channels 82 (see FIG. 11) connecting each reagent well 72 with all of the primary fluid channels 76, and a secondary fluid channel 78 extending from each primary fluid channel 76 and terminating at a fluid delivery port 84 at the delivery interface 86 where it is coupled with an inlet port (not numbered in FIG. 6) of the microfluidic chip 18. Sample is input through the sample well 68 and is delivered to the associated primary fluid channel 76 via the sample delivery channel 80 (See FIGS. 7-9). As the sample flows through the primary fluid channel 76, it is mixed with reagents/primers delivered to the primary fluid channel 76 from selected reagent wells 72 via reagent delivery channels 82 (see FIGS. 11-12). Prior to the primary fluid channel 76 reaching the vent well 70, the secondary fluid channel 78 splits off and a percentage of the sample/reagent mixture flows, via the primary fluid channel 76, to the vent well 70 and a percentage of the sample/reagent mixture flows, via the secondary fluid channel 78, into the microfluidic process channel of the microfluidic chip 18 for, e.g., PCR and thermal melt analysis.

In the embodiment shown, the 96-well interface cartridge 62 lacks fluid removal channels coupled to outlet ports of the microfluidic process channels 24 of the microfluidic chip 18 and waste collection wells configured to collect waste fluids conveyed from the microfluidic chip 18 by the fluid removal channels. Alternative configurations of a 96-well (or other number of wells) interface cartridge in which fluid removal channels and waste collection wells are contemplated as embodying aspects of the present invention.

Figure 10:
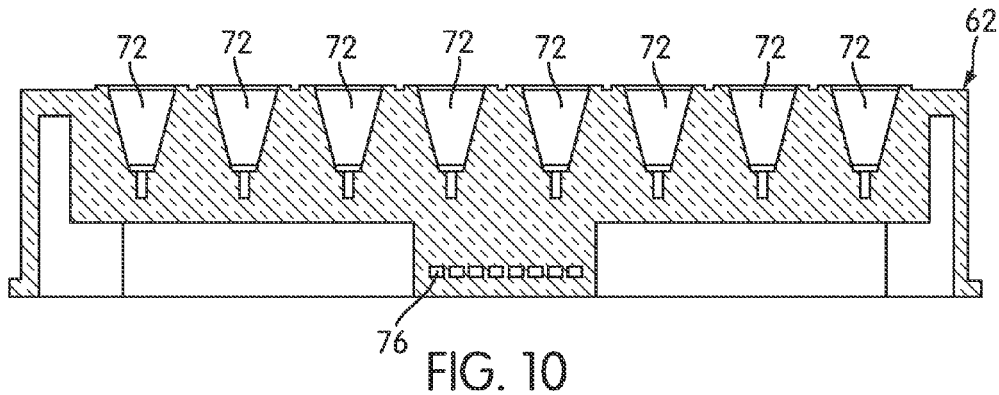
FIG. 10 is a cross-sectional view of the interface cartridge of FIG. 5, taken along the line 10-10.

FIG. 10 is a cross section through the reagent wells 72 showing the conical shape of each of the wells in accordance with one exemplary embodiment. It is also contemplated that wells having other shapes may be used as well.

Figure 11:
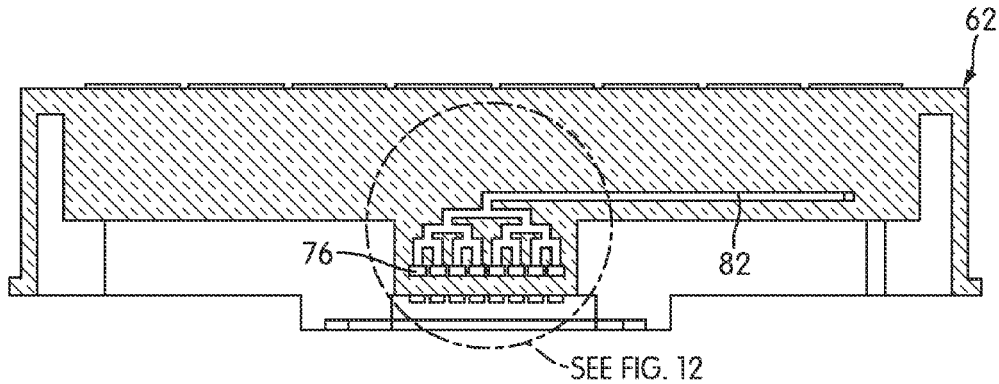
FIG. 11 is a cross-sectional view of the interface cartridge of FIG. 5, taken along the line 11-11.
Figure 12:
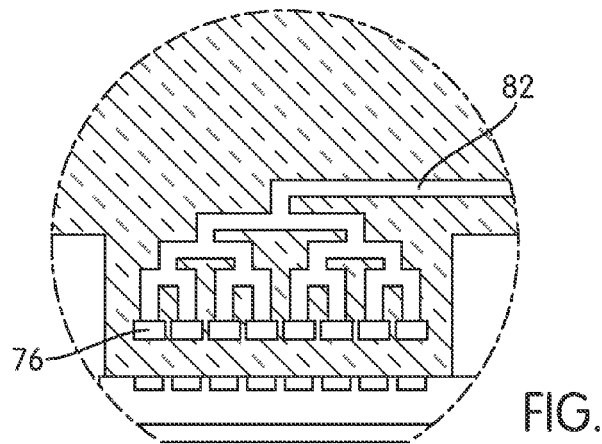
FIG. 12 is a detail of a portion of the cross sectional view of FIG. 11.
Figure 13:
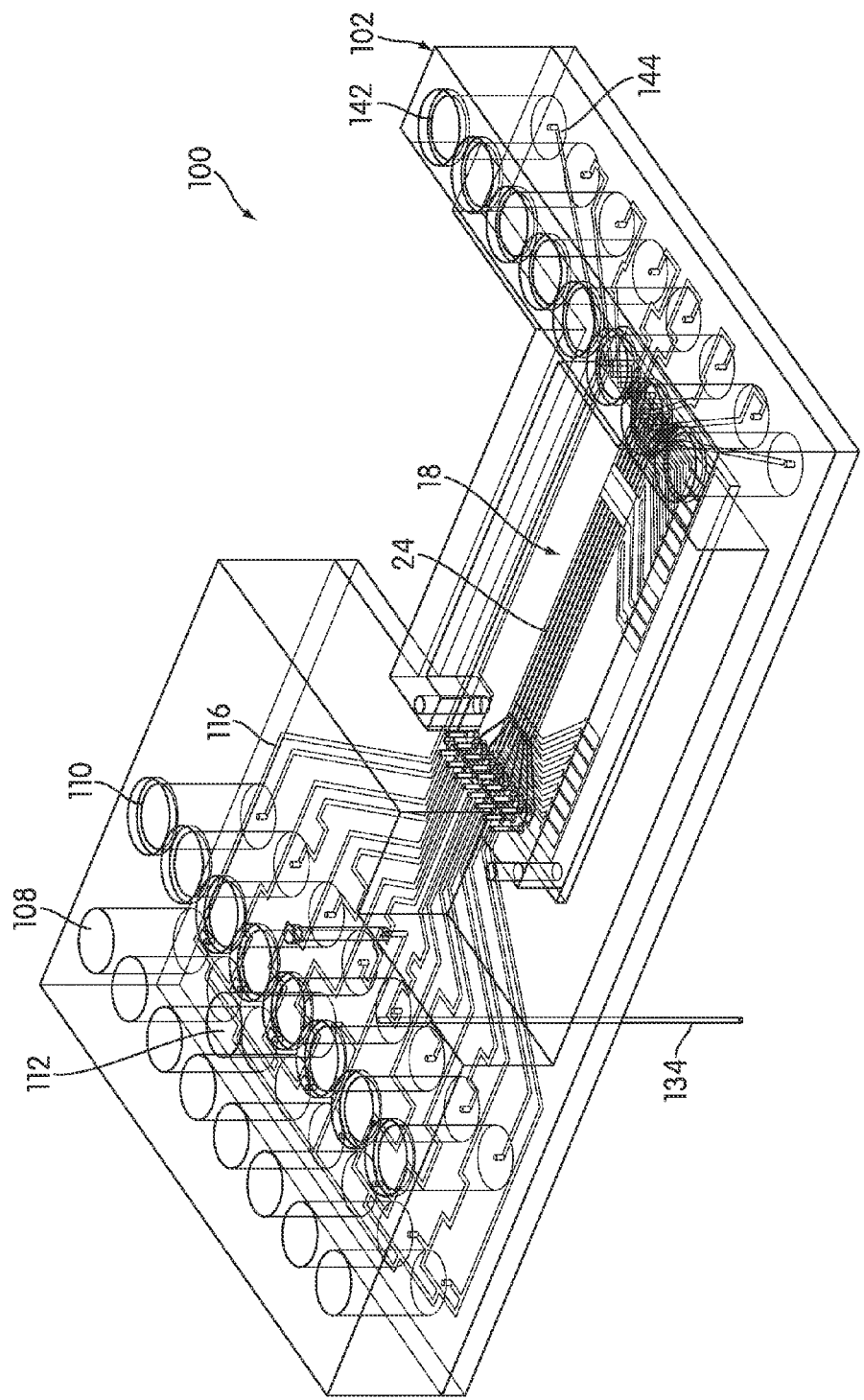
FIG. 13 is a perspective view of an alternative configuration of an interface cartridge coupled to a microfluidic chip having a plurality of process channels, wherein the interface cartridge includes a plurality of sample input wells, a common reagent well, a plurality of vent wells, a plurality of waste wells, and a sipper tube disposed beneath the interface cartridge.

FIG. 11 is a cross section showing a reagent delivery channel 82 from a single reagent well. FIG. 12 is an enlarged detailed view of a portion of the reagent delivery channel. In the illustrated embodiment, the reagent delivery channel divides three times so that a single channel from a single well can flow into each of the eight primary fluid channels 78. This configuration of channels may be referred to as "h-channels."

In one embodiment, the 96 well interface cartridge 62 may be made from Somos® 11122 WaterShed™ XC 11122 SLA resin. Of course, other suitable materials may be used as well.

In one embodiment, microfluidic chip 18 is supported with respect to the interface cartridge 62 by a chip support platform 90 that is fixed relative to the cartridge 62 and having an opening 92 formed therein so as to enable optical detection of properties of fluid flowing through portions of the microfluidic process channels 24 above the opening 92. See FIG. 26

Figure 26:
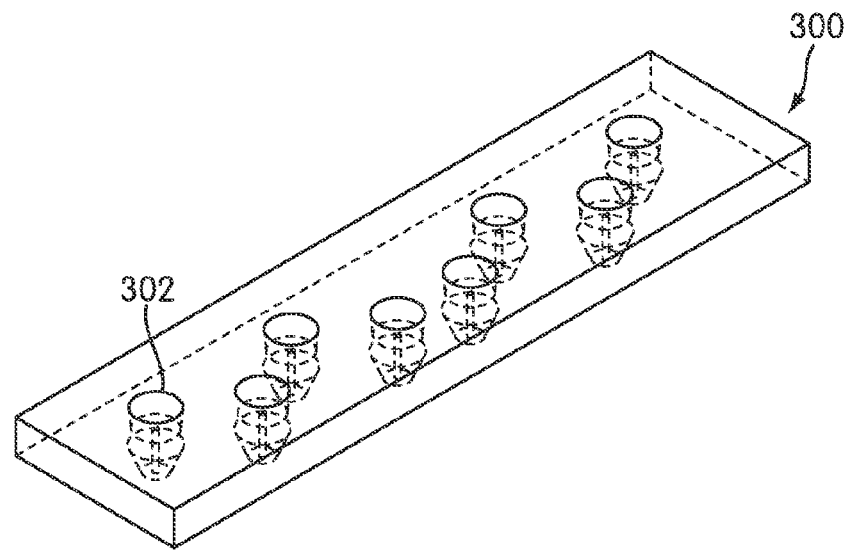
FIG. 26 is a perspective view of an interface gasket for use between an interface cartridge and a microfluidic chip.
Figure 27:
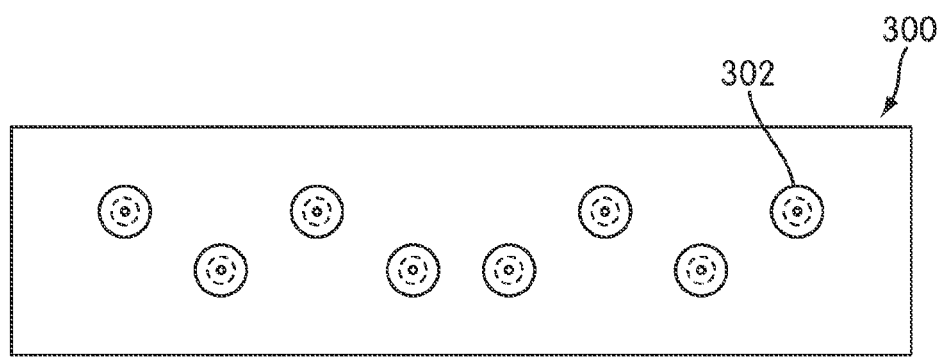
FIG. 27 is a top plan view of the interface gasket.
Figure 28:
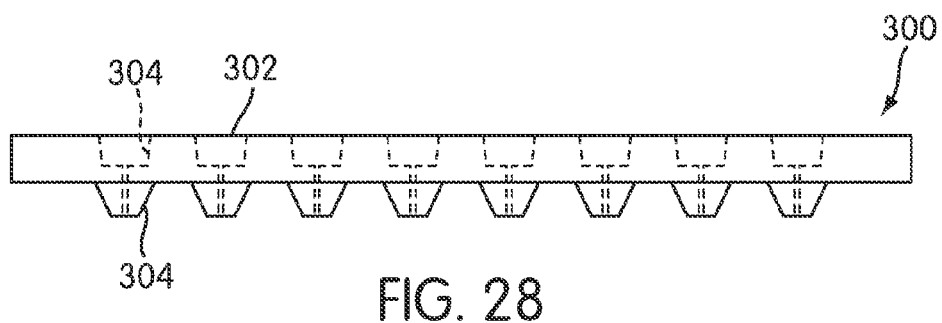
FIG. 28 is a side view of the interface gasket.

Details of one embodiment of a connection gasket are shown in FIGS. 26-28. The gasket, represented by reference number 300, includes a plurality of ports 302. In the illustrated embodiment, gasket 300 includes eight ports 302 corresponding to the eight microfluidic process channels of the microfluidic chip. Each port 302 includes a tapered, circular recess 304 formed in the top of the gasket 300 and a frusto-conical nipple 306 projecting from the bottom of the gasket 302. A circular projection surrounding each of the fluid delivery ports 84 extends into the recess 304. In the illustrated embodiment, the ports 302 are arranged in two parallel lines whereby the ports 302 of one line are staggered with respect to the ports 302 of the other line. In other embodiments, the ports 302 can be arranged in two or more staggered or non-staggered lines, or the ports 302 can be arranged in a single line. The gasket can be made of an elastomeric polymer or other suitable material, or the gasket can be replaced by an adhesive material, such as curable liquid adhesive, single sided tape, double sided tape or adhesive transfer tape. Other materials suitable for the gasket or for use as an adhesive are known to those of skill in the art.

Another assembly embodying aspects of the present invention is indicated by reference number 100 in FIGS. 13-17. Assembly 100 includes an interface cartridge 102 to which is coupled a microfluidic chip 18. Interface cartridge 102 has similar design concepts to the 96-well interface chip 62 described above. Both interface cartridges 62 and 102 are designed with microfluidic control, mixing, and delivery functionality such that random access assays can be delivered to the microfluidic process channels 24 of the microfluidic chip 18. Unlike the 96-well interface cartridge 62 described above, random reagent access is provided by a sipper tube 134 attached to the bottom side 106 of the interface cartridge 102 (see FIG. 15) for sipping reagents from, for example, a microplate (not shown) positioned below the assembly 100.

As described above, and shown in FIG. 15, customized gaskets 140, 148 are used to connect and seal the interface cartridge 102 with the microfluidic chip 18 at a delivery interface 138 and a waste interface 146, respectively. Recesses 141, 149 conforming in shape to the gaskets 140, 148, respectively, may be formed in the bottom side 106 of the interface cartridge 102 for receiving the gaskets 140, 148 (see FIG. 14).

Figure 14:
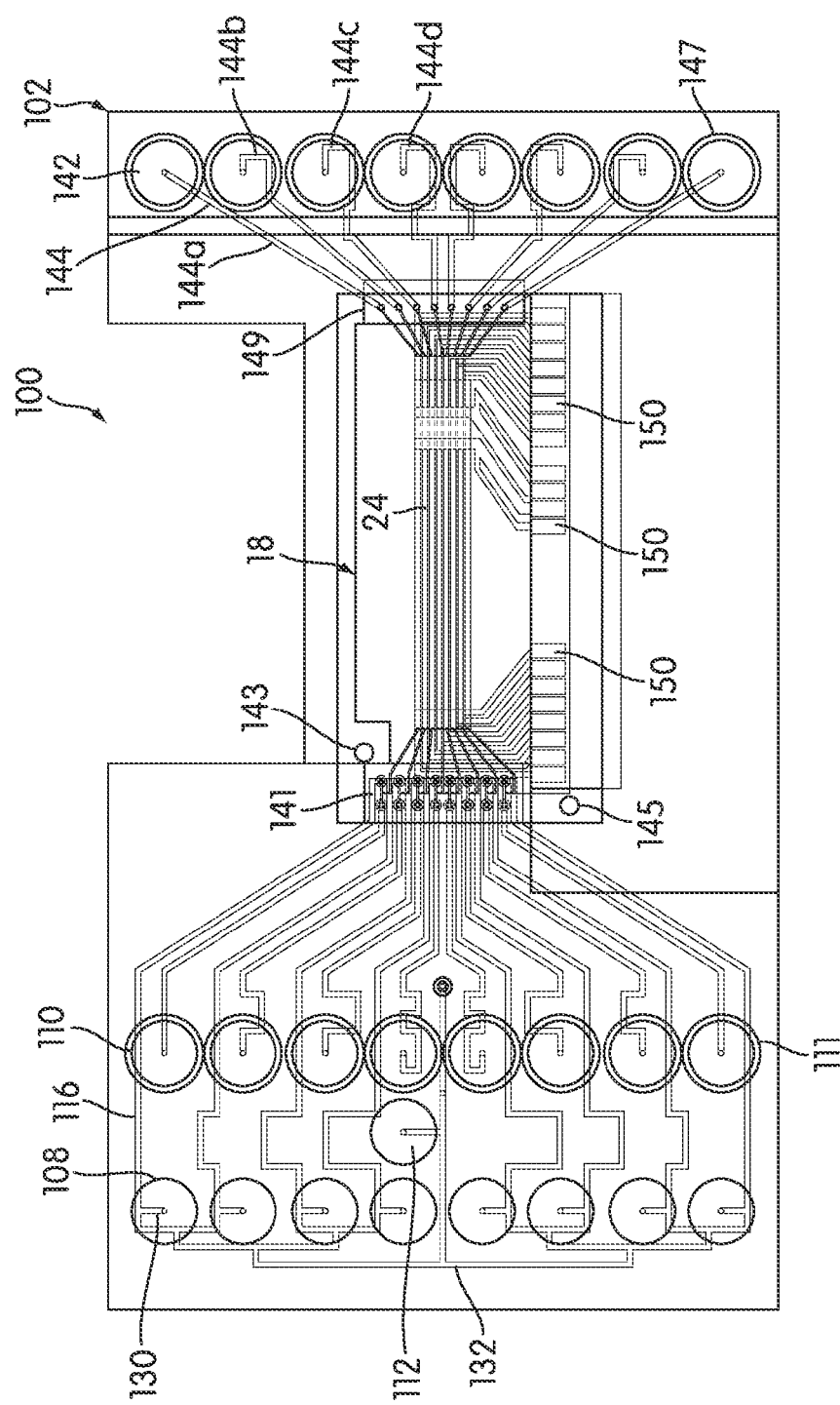
FIG. 14 is a top plan view of the interface cartridge of FIG. 13.
Figure 15:
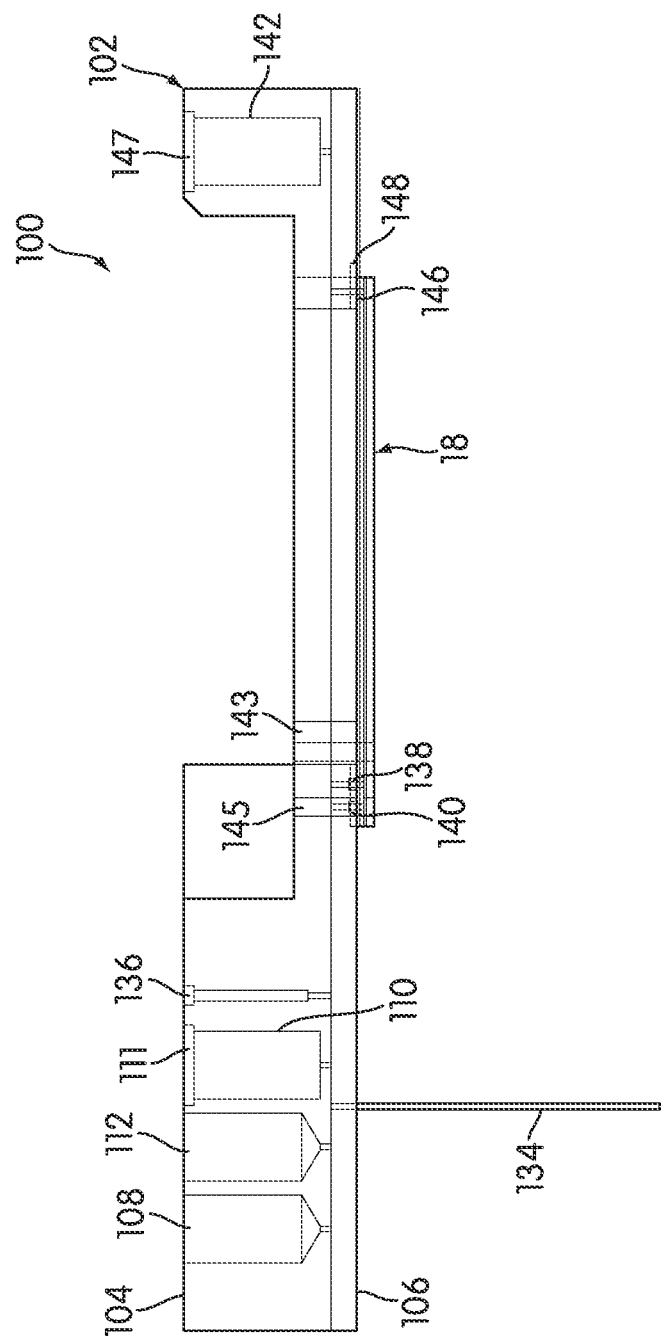
FIG. 15 is a side view of the interface cartridge/microfluidic chip arrangement shown in FIG. 14.
Figure 16:
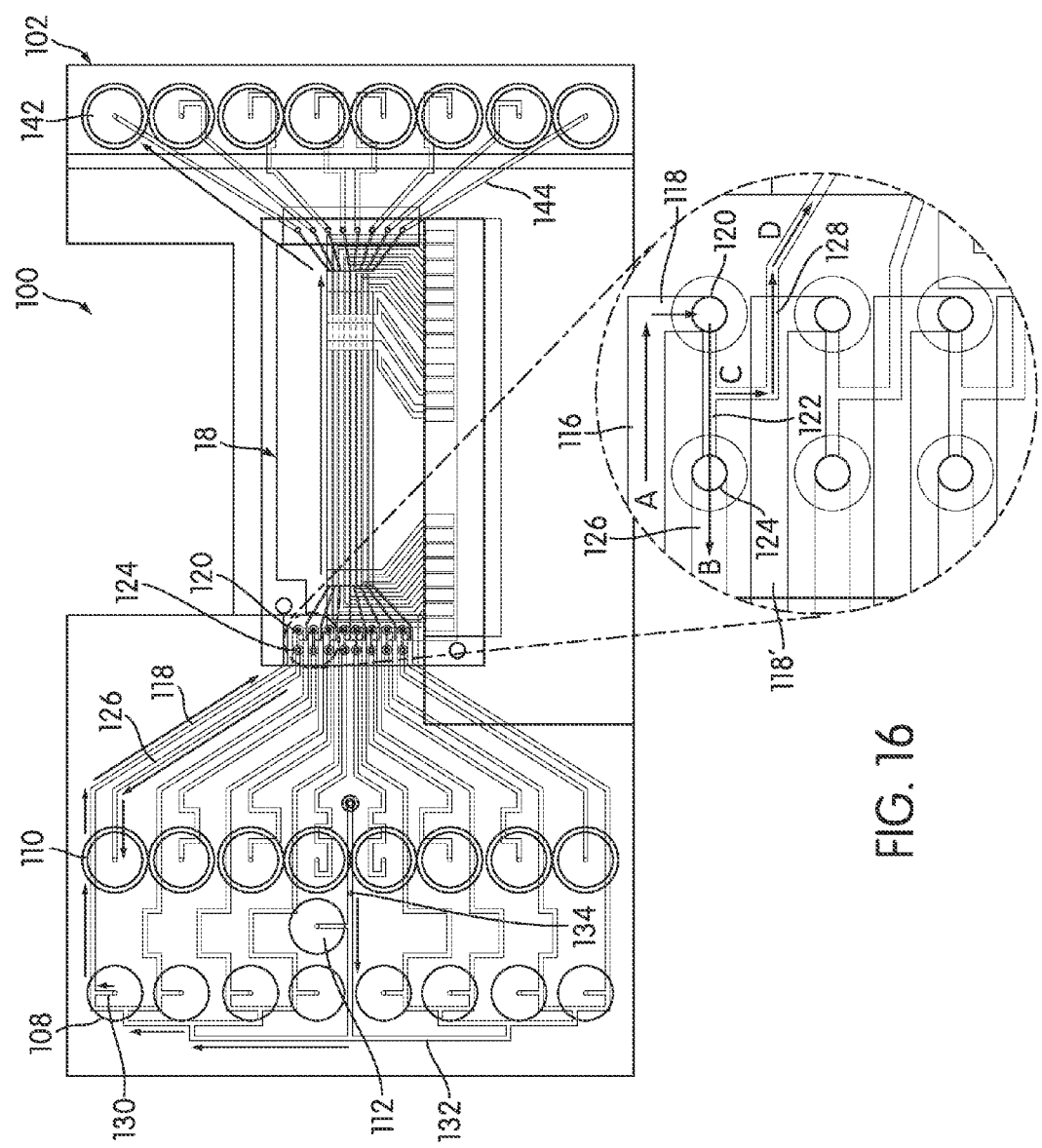
FIG. 16 is a plan view of the interface cartridge and microfluidic chip shown in FIG. 13 with arrows superimposed thereon showing fluid flow directions and wherein a portion of the interface coupling between the interface cartridge and the microfluidic chip is shown in enlarged detail.
Figure 17:
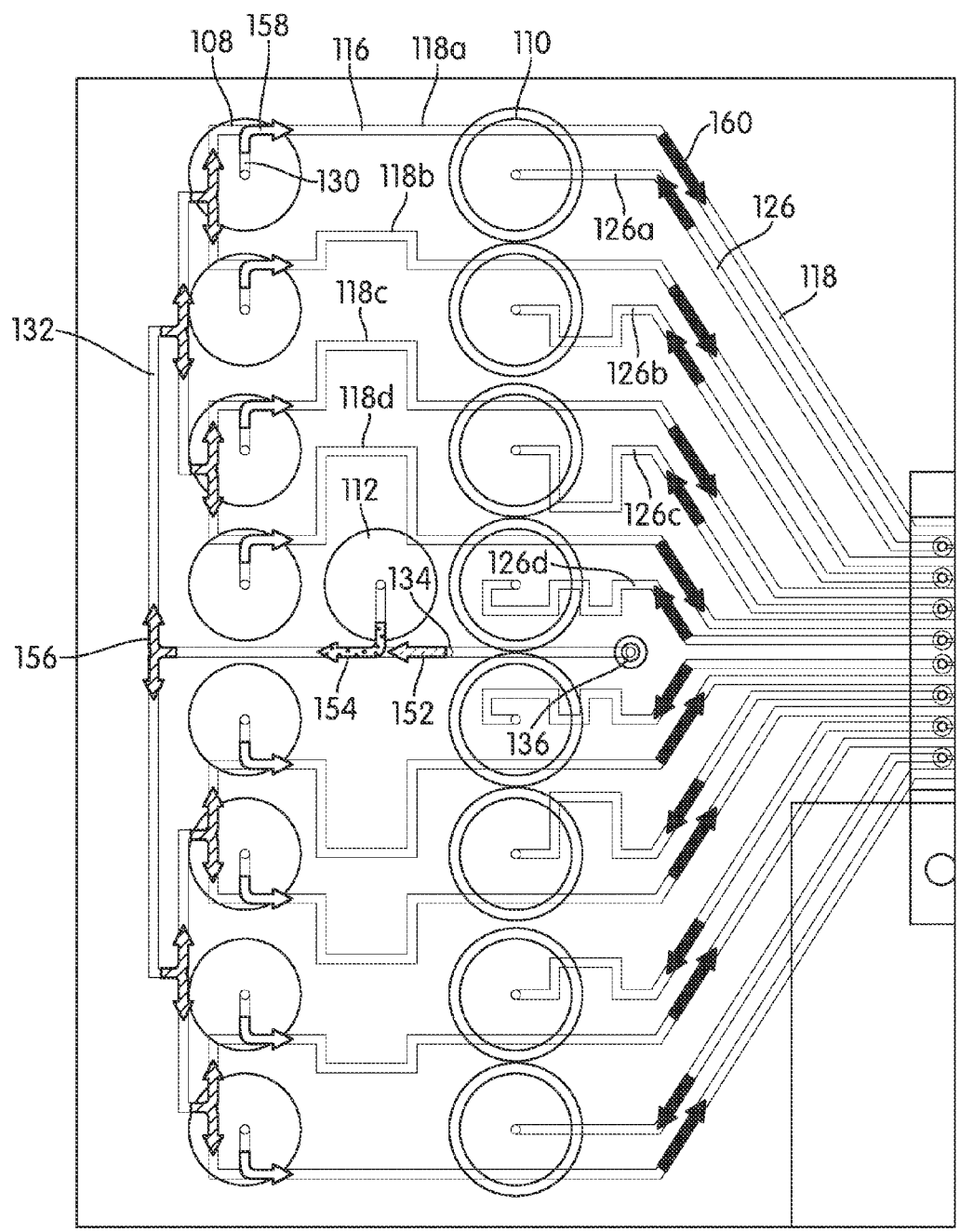
FIG. 17 is a partial plan view of the interface cartridge shown in FIGS. 13-16 with arrows superimposed thereon showing fluid flow directions in the ancillary channels.

The design layout of the interface cartridge 102 is illustrated in FIGS. 14, 16 and 17. The first row of wells formed in the top side 104 of the interface cartridge 102 comprises patient sample wells 108 in which a user would add the samples to be tested. A common reagent well 112 contains a reagent that is common to all assays to be performed in the microfluidic chip 18. A row of vent wells 110 is provided to collect excess sample and reagent fluids. A row of waste collection wells 142 is provided to collect the remains of the assay mixture removed from the microfluidic process channels 24 of the microfluidic chip 18. The sipper tube 134 is used to draw assay reagents, such as PCR reagents, from a micro-well plate disposed below the assembly 100. A vacuum assist connection hole 136 is provided to counteract hydrostatic pressure of the sipper tube 134 (see FIG. 15). Electrical connection pads 150 connect channel-heating elements within the microfluidic chip 18 to an external power source.

Interface cartridge 102 includes fluid delivery channels configured to convey fluids (sample, reagents, etc.) from the wells 108, 110, 112 and sipper tube 134 to the microfluidic process channels 24 of the microfluidic chip 18. More specifically, the fluid delivery channels include primary fluid channels 116 connecting each sample well 108 with one vent well 110. A sample delivery channel 130 connects each sample well 108 with each associated primary fluid channel 116. In the illustrated embodiment, interface cartridge 102 includes eight primary channels 116, corresponding to eight associated sample wells 108 and vent wells 110. Reagent delivery channels 132 connect the common reagent well 112 and the sipper tube 134 with all primary fluid channels 116. In one illustrative embodiment, the reagent delivery channels 132 divides three times (forming h-channels), so that the single channel from the common reagent well 112 and the sipper tube 134 is in fluid-communication with all eight primary fluid channels 116. Fluid removal channels 144 connect each waste collection well 142 to an associated one of the microfluidic process channels 24.

Each primary fluid channel 116 comprises a delivery leg 118 conveying a mixture of sample and reagent toward the delivery interface coupling the interface cartridge 102 with the microfluidic chip 18 and a return leg 126 conveying excess fluid mixture (i.e., that portion of the fluid mixture that is not drawn into the associated microfluidic process channel 24) back to the vent well 110. Arrows shown in the top illustration in FIG. 16 show the general directions of fluid flow through the reagent delivery channels 132 and the delivery legs 118 and the return legs 126 of the primary fluid channels 116.

In accordance with one embodiment, FIG. 17 illustrates that each of the delivery legs 118a, 118b, 118c, 118d progressing from the lateral perimeter of cartridge body toward the center of the cartridge body includes an increasingly large deviation from a direct, straight-line path. This results in each of the delivery legs 118a, 118b, 118c, 118d of the primary fluid channels 116 having a substantially identical length, so that fluid flowing through the delivery legs will arrive at the microfluidic chip 18 at substantially the same time. However, delivery legs having other and different lengths may be used.

Similarly, each of the return legs 126a, 126b, 126c, 126d progressing from the lateral perimeter of cartridge body toward the center of the cartridge body includes an increasingly large deviation from a direct, straight-line path. This results in each of the return legs 126a, 126b, 126c, 126d of the primary fluid channels 116 having a substantially identical length, so that fluid flowing through the return legs will arrive at the vent wells 110 at substantially the same time. Also, each of the fluid removal channels 144a, 144b, 144c, 144d progressing from the lateral perimeter of cartridge body toward the center of the cartridge body includes an increasingly large deviation from a direct, straight-line path. This results in each of the fluid removal channels 144a, 144b, 144c, 144d having a substantially identical length (see FIG. 16).

Exemplary dimensions of the interface cartridge 102 are 38 mm wide×67.8 mm long with a total thickness of 6 mm. Exemplary well diameter is 3.7 mm. The distance between all channels in the interface cartridge 102 is preferably maintained at 200 µm. One of skill in the art will recognize that such dimensions are only exemplary and alternative dimensions are envisioned and encompassed by the present invention.

The lower illustration in FIG. 16 is a detail showing the transition between the delivery leg 118 and the return leg 126 of each primary fluid channel 116. The delivery leg 118 includes a vertical leg 120 at its terminal end. The vertical leg 120 comprises a fluid connection hole extending to a fluid delivery port at the bottom 106 of the interface cartridge 102. Similarly, the return leg 126 includes a vertical leg 124 at its terminal end. The vertical leg 124 comprises a fluid connection hole extending to a fluid return port at the bottom 106 of the interface cartridge 102. The vertical leg/fluid connection hole 120 and the vertical leg fluid connection hole 124 have exemplary dimensions of 250 µm. The vertical leg/fluid connection hole 120 and the vertical leg fluid connection hole 124 connect at the delivery interface 138 to corresponding inlet ports formed in the microfluidic chip 18. The inlet ports of the microfluidic chip 18 corresponding to connection holes 120, 124 are connected to each other by a connector leg 122 formed in the microfluidic chip 18. A secondary flow channel 128 formed in the microfluidic chip 18 extends from the connector leg 122 (preferably from a point generally bisecting the connector leg 122) to one of the microfluidic process channels 24 of the microfluidic chip 18.

Fluid conveyed by the delivery leg 118 flows in the direction indicated by arrow "A". From the delivery leg 118, the fluid encounters vertical leg 120 extending down (into the page of FIG. 16). Fluid then flows along the connector leg 122 before it encounters the second vertical leg 124, extending up to and connecting with return leg 126 along which fluid flows in the direction indicated by arrow "B" toward the vent well 110. Flows A and B are driven and controlled by selective application of a vacuum at the vent wells 110, or by other means known to those skilled in the art. To facilitate application of a vacuum, vent wells 110 preferably include an o-ring groove 111 surrounding their openings for receiving an o-ring to provide a substantially air-tight seal between the vacuum source and the interface cartridge 102 at the vent wells 110.

A portion of the fluid flowing into the connector leg 122 from the delivery leg 118 and the first vertical leg 120 of the primary fluid channel 116 is diverted into the secondary flow fluid channel 128 (arrow "C") and is conveyed by the secondary flow channel 128 in the direction indicated by arrow "D" toward the microfluidic process channel 24. Flows C and D are driven and controlled by selective application of a vacuum at the waste collection wells 142. To facilitate application of a vacuum, waste collection wells 142 preferably include an o-ring groove 147 surrounding their openings for receiving an o-ring to provide a substantially air-tight seal between the vacuum source and the interface cartridge 102 at the waste collection wells 142.

Because the connector leg 122 is below the plane of the delivery leg 118 and the return leg 126, the connector leg 122 and the secondary fluid flow channel 128 is positioned below the return leg 126' of the adjacent primary fluid flow channel.

The flow pattern of the interface cartridge 102 and microfluidic chip 18 of assembly 100 is illustrated in FIG. 16. Specific reagents move into the interface cartridge 102 through the sipper tube 134 (vacuum assist connection 136 is provided to counteract hydrostatic pressure of sipper tube 134). Reagents common to all PCR reactions are added into the common reagent well 112. Reagents stream equally into the eight primary fluid flow channels 116 through h-branching of the reagent delivery channel 132. Patient DNA, or other sample, is added to each of the eight sample wells 108. The mixture (sample and reagents) flows in the delivery leg 118 in the direction indicated by arrow "A" in FIG. 16, through the connector leg 122, and back into the vent well 110 via the return leg 126 in the direction indicated by arrow "B" in FIG. 16. Vent wells 110 include a vacuum fitting on top for drawing fluid. As is also shown in FIG. 16, a portion of the flow in the connector leg 122, A to B, is drawn into the secondary fluid flow channel 128 and toward the microfluidic process channel 24 of the microfluidic chip 18, C to D, from vacuum driven flow at the waste collection wells 142 (vacuum fitting on top of waste collection well 142). The interface cartridge 102 serves two functions: mixing regents and continuous flow (left half) and moving mixed reagents into the microfluidic chip for analysis by discontinuous flow (right half). In accordance with one embodiment, the interface cartridge 102 also has 1 mm diameter holes 143, 145 for the placement of alignment pins. Alignment pins can be used to align the interface cartridge with the microfluidic chip, or to align the assembly of the interface cartridge and the microfluidic chip in an analysis device.

FIG. 17 shows a further schematic of the movement of fluid within the interface cartridge 102 in accordance with one embodiment. Assay specific reagents move into interface cartridge 102 through sipper tube 134, as represented by arrow 152 with dashed cross hatching, and flows into undivided reagent delivery channel 132. Reagent common to all assays, as represented by arrow 154 with stippling, flows from common reagent well 112 and into the undivided reagent delivery channel 132. The reagent(s) flowing through reagent delivery channel 132 are split 3 times to form eight identical streams, as represented by arrows 156 with solid cross hatching, flowing in the divided reagent delivery channel 132 (a reagent flow region). Patient DNA sample is added to each of the eight primary fluid delivery channels 116, as represented by arrows 158 with no cross hatching or stippling (a sample flow region). Solid black arrows 160 represent mixed sample and reagents flowing in the delivery legs 118 and the return legs 126 of the primary fluid channels 116 (a mixing region).

Figure 16A:
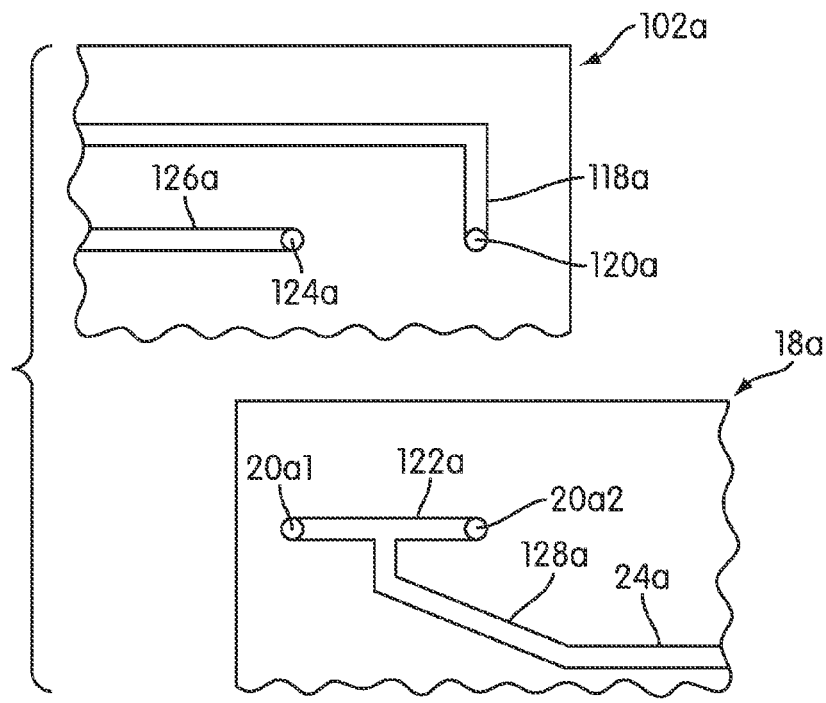
FIG. 16A is partial plan view of an interface cartridge and microfluidic chip showing one embodiment of a fluidic interface between the interface cartridge and the microfluidic chip.

FIG. 16A is partial plan view of an interface cartridge 102a and microfluidic chip 18a showing one embodiment of a fluidic interface between the interface cartridge and the microfluidic chip. The embodiment of FIG. 16A corresponds to the embodiment shown in FIGS. 13-16 and described above. FIG. 16A is a partial view showing only a single fluid delivery channel and microfluidic process channel, but the assembly may include a plurality of fluid delivery channels and microfluidic process channels and may or may not include the same number of each type of channels. Interface cartridge 102a includes at least one fluid delivery channel including a delivery leg 118a which terminates at a vertical fluid connection hole 120a and a return leg 126a which extends from a vertical connection hole 124a. Holes 120a and 124a extend to the bottom of the interface cartridge 102a. Microfluidic chip 18a includes at least one first fluid connection port 20a1 and a second fluid connection port 20a2 connected by a connector leg 122a. A secondary flow channel 128a formed in the microfluidic chip 18a extends from the connector leg 122a to the microfluidic process channel 24a. When the interface cartridge 102a and the microfluidic chip 18a are coupled, the vertical connection hole 120a is in fluid-communication with second fluid connection port 20a2, and the vertical connection hole 124a is in fluid-communication with first fluid connection port 20a1. A portion of the fluid flowing from delivery leg 118a, through the connecter leg 122a, and toward the return leg 126a can be drawn into the microfluidic process channel 24a through the secondary flow channel 128a.

Figure 16B:
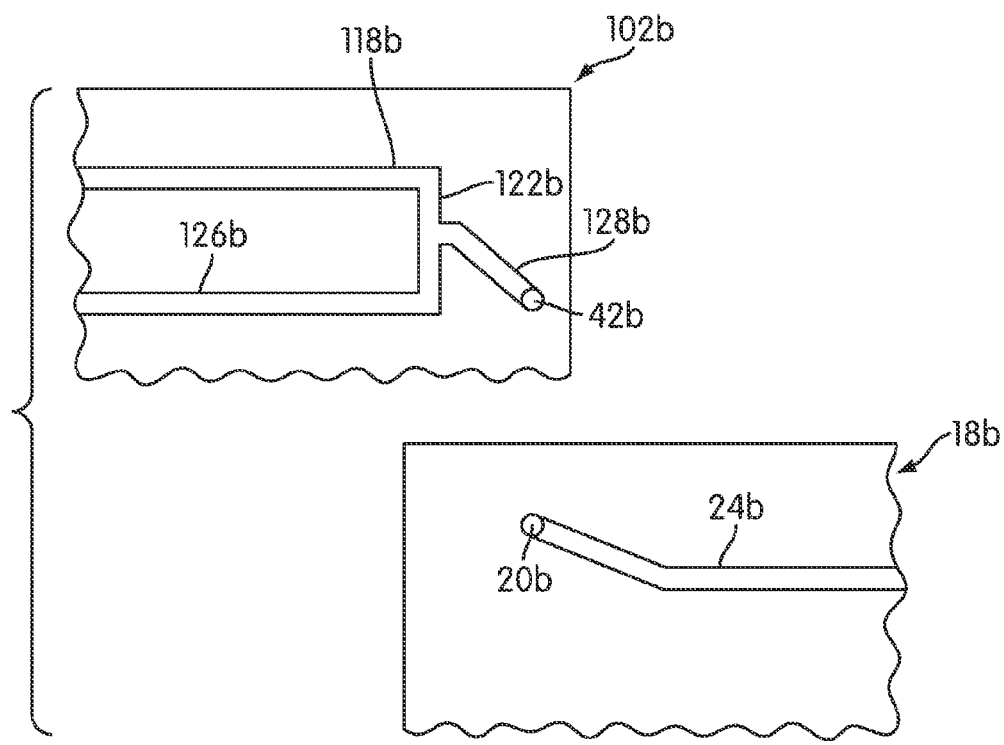
FIG. 16B is partial plan view of an interface cartridge and microfluidic chip showing another embodiment of a fluidic interface between the interface cartridge and the microfluidic chip.
Figure 16C:
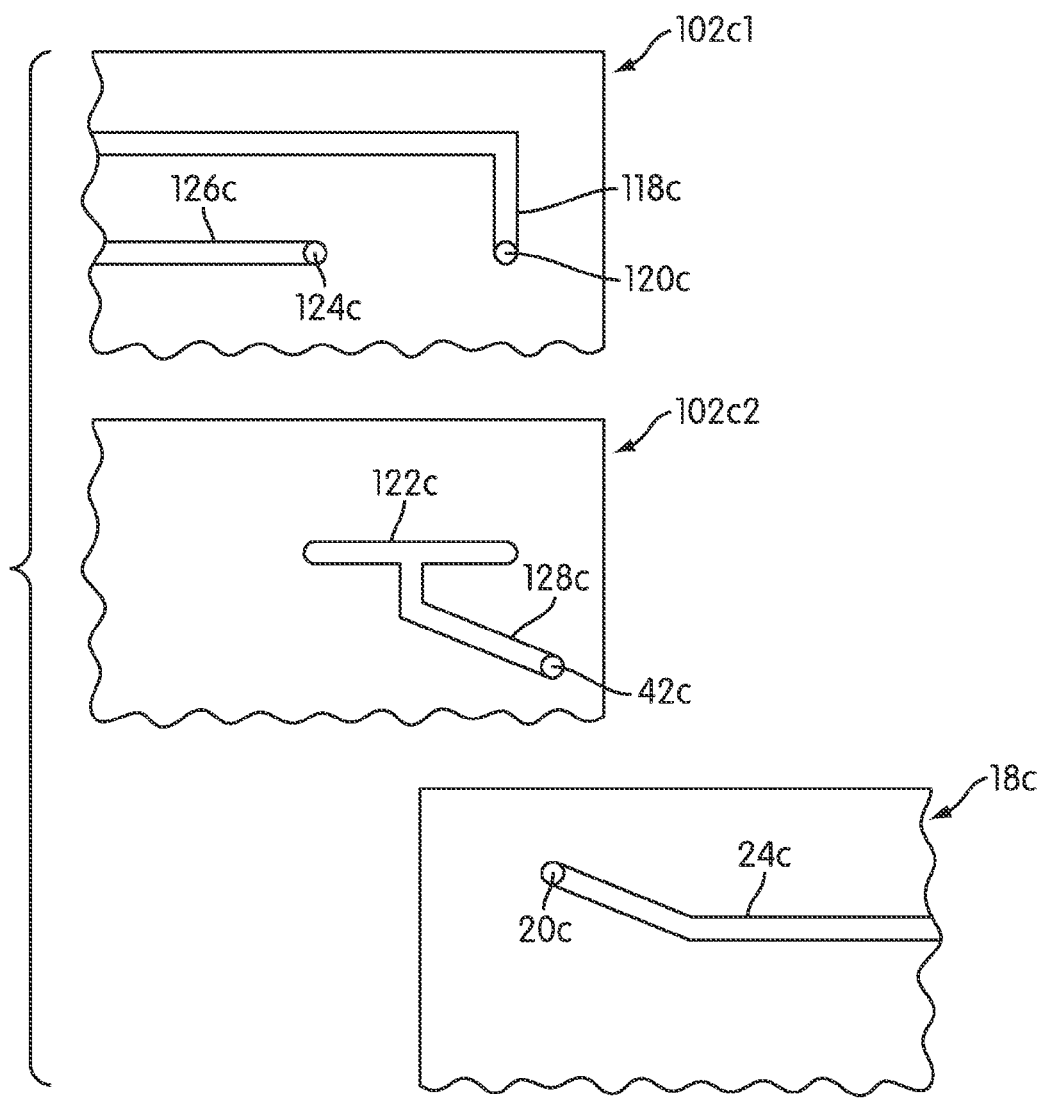
FIG. 16C is partial plan view of a multi-layer interface cartridge and microfluidic chip showing a further embodiment of a fluidic interface between the interface cartridge and the microfluidic chip.

FIG. 16B is partial plan view of an interface cartridge 102b and microfluidic chip 18b showing another embodiment of a fluidic interface between the interface cartridge and the microfluidic chip. FIG. 16B is a partial view showing only a single fluid delivery channel and microfluidic process channel, but the assembly may include a plurality of fluid delivery channels and microfluidic process channels and may or may not include the same number of each type of channels. Interface cartridge 102b includes at least one fluid delivery channel including a delivery leg 118b and a return leg 126b connected by a connector leg 122b formed in the interface cartridge 102b. Microfluidic chip 18b includes at least one fluid inlet port 20b at a proximal end of a microfluidic process channel 24b. A secondary flow channel 128b formed in the interface cartridge 102b extends from the connector leg 122b to a fluid delivery port 42b. When the interface cartridge 102b and the microfluidic chip 18b are coupled, fluid delivery port 42b is in fluid-communication with the fluid inlet port 20b. A portion of the fluid flowing from delivery leg 118b, through the connecter leg 122b, and toward the return leg 126b can be drawn into the microfluidic process channel 24b through the secondary flow channel 128b FIG. 16C is partial plan view of an interface cartridge comprising first layer 102c1 and 102c2 and a microfluidic chip 18c showing a further embodiment of a fluidic interface between the interface cartridge and the microfluidic chip. FIG. 16C is a partial view showing only a single fluid delivery channel and microfluidic process channel, but the assembly may include a plurality of fluid delivery channels and microfluidic process channels and may or may not include the same number of each type of channels. First layer 102c1 includes at least one a delivery leg 118c which terminates at a vertical fluid connection hole 120c and at least one return leg 126c which extends from a vertical connection hole 124c. Holes 120c and 124c extend to the bottom of layer 102c1. Second layer 102c2 includes a connector leg 122c and a secondary flow channel 128c extending from the connector leg 122c and terminating at fluid delivery port 42c. Microfluidic chip 18c includes at least one fluid inlet port 20c at a proximal end of a microfluidic process channel 24c. When the first layer 102c1 and the second layer 102c2 are assembled, the vertical connection hole 120a is in fluid-communication with one end of the connector leg 122c and the vertical connection hole 124c is in fluid-communication with the opposite end of the connector leg 122c. When the interface cartridge 102c1/102c2 is coupled to the microfluidic chip 18c, the fluid delivery port 42c is in fluid-communication with the fluid inlet port 20c. A portion of the fluid flowing from delivery leg 118c, through the connecter leg 122c, and toward the return leg 126c can be drawn into the microfluidic process channel 24c through the secondary flow channel 128c.

Another assembly embodying aspects of the present invention is indicated by reference number 180 in FIGS. 18-22. Assembly 180 includes an interface cartridge 182 to which is coupled a microfluidic chip 18. As described above, customized gaskets (not shown) may be used to connect and seal the interface cartridge 182 with the microfluidic chip 18 at a delivery interface and a waste interface. Unlike the 96-well interface cartridge 102 described above, reagents are provided by a pre-interface chip 204 rather than a sipper tube. Pre-interface chip 204 includes internal reservoirs and channels for storing and delivering common and assay-specific reagent to the interface cartridge 182 via a reagent inlet channel 196 connected to reagent delivery channels 194.

Figure 18:
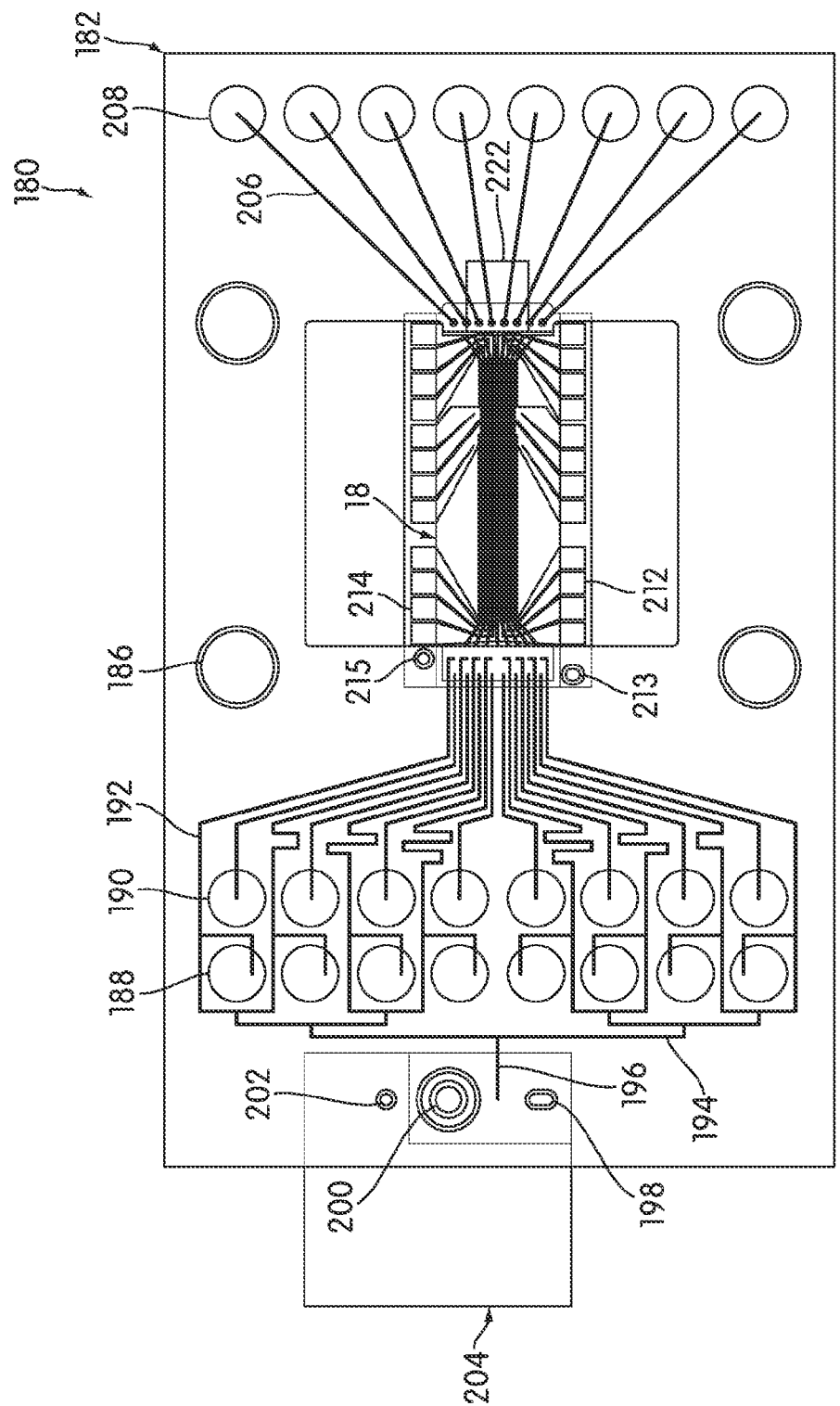
FIG. 18 is a plan view of an alternate embodiment of an interface cartridge shown coupled to a microfluidic chip having a plurality of process channels and further showing a preprocessing chip coupled to an input port of the interface cartridge.
Figure 19:
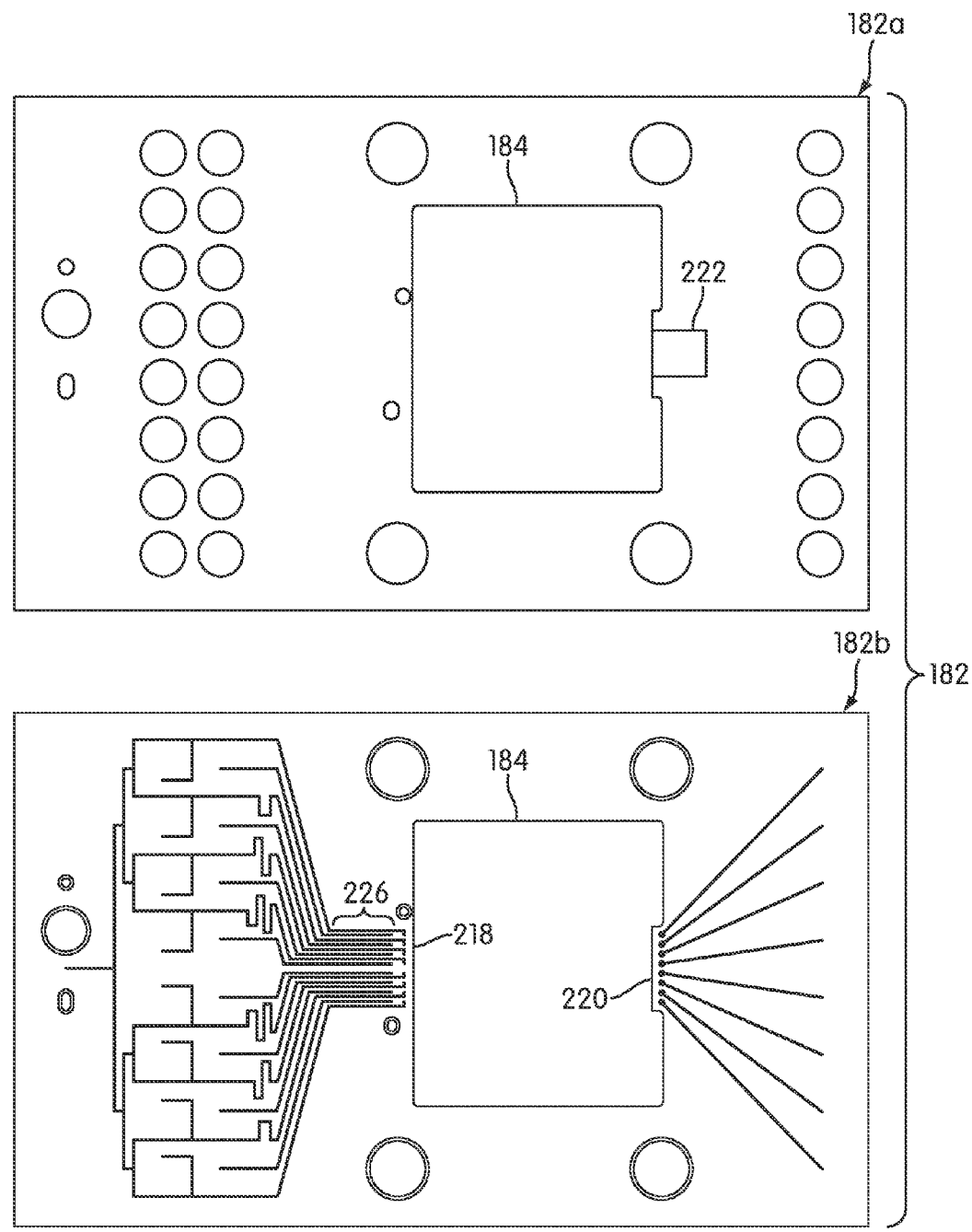
FIG. 19 is a plan view of different layers of the multilayer structure embodied in the interface cartridge shown in FIG. 18.
Figure 20:
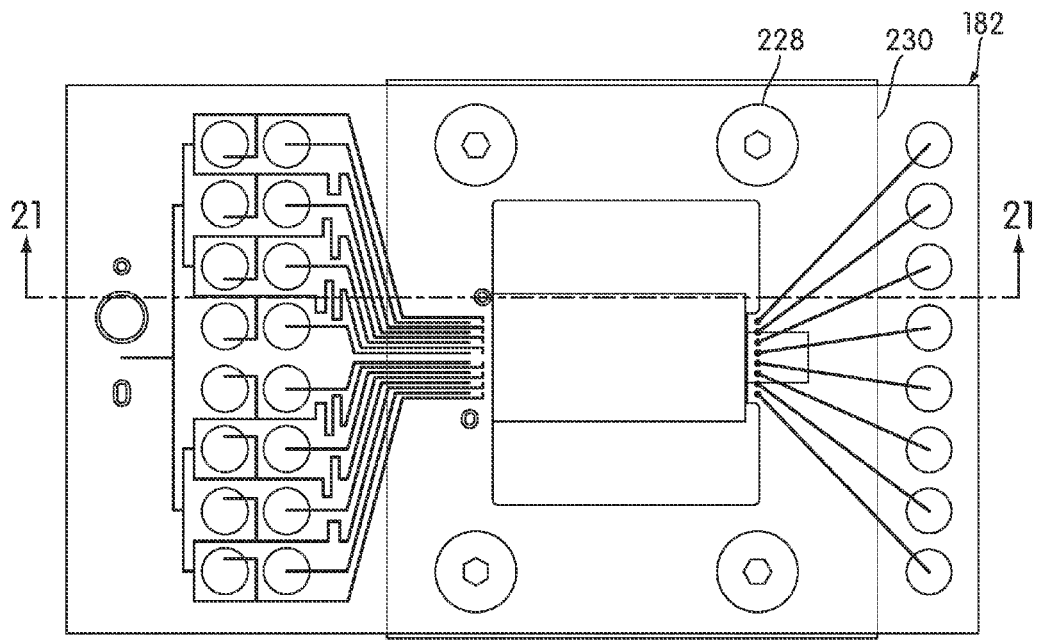
FIG. 20 is a plan view of the interface cartridge shown in FIG. 18 with a microfluidic chip coupled therewith and a chip-holding bracket supporting the microfluidic chip with respect to the interface cartridge.

The design layout of the interface cartridge 182 is illustrated in FIGS. 18 and 19. The first row of wells formed in the top side of the interface cartridge 182 comprises patient sample wells 188 in which a user would add the samples to be tested. A row of vent wells 190 is provided to collect excess sample and reagent fluids. A row of waste collection wells 208 is provided to collect the remains of the assay mixture removed from the microfluidic process channels 24 of the microfluidic chip 18. Electrical connection pads 212, 214 connect channel-heating elements within the microfluidic chip 18 to an external power source. In this regard, the design shown in FIGS. 18-22 has been altered to accommodate a different style microfluidic chip 18 wherein the interface cartridge 182 now provides access to both rows of microfluidic chip electrical contact pads on both sides of the chip, as compared with providing contact to only one side of the microfluidic chip as in the previously-described embodiment.

Interface cartridge 182 includes fluid delivery channels configured to convey fluids (sample, reagents, etc.) from the wells 188, 190 and pre-interface chip 204 to the microfluidic process channels 24 of the microfluidic chip 18. More specifically, the fluid delivery channels include primary fluid channels 192 connecting each sample well 188 with one vent well 192. A sample delivery channel connects each sample well 188 with each associated primary fluid channel 192. In the illustrated embodiment, interface cartridge 182 includes eight primary channels 192, corresponding to eight associated sample wells 188 and vent wells 190. Reagent delivery channels 194 connect the pre-interface chip 204 with all primary fluid channels 192. Fluid removal channels 206 connect each waste collection well 208 to an associated one of the microfluidic process channels 24.

As with the previously-described embodiment, each primary fluid channel 192 comprises a delivery leg conveying a mixture of sample and reagent toward the delivery interface coupling the interface cartridge 182 with the microfluidic chip 18 and a return leg conveying excess fluid mixture (i.e., that portion of the fluid mixture that is not drawn into the associated microfluidic process channels 24) back to the vent well 190. Flow through the primary fluid channels 192 from the sample wells 188 to the vent wells 190 is driven and controlled by selective application of a vacuum at the vent wells 190.

Note that delivery legs of the primary fluid channels 192 progressing from the lateral perimeter of cartridge body toward the center of the cartridge body include an increasingly large deviation from a direct, straight-line path. This results in each of the delivery legs of the primary fluid channels 192 having a substantially identical length, so that fluid flowing through the delivery legs will arrive at the microfluidic chip 18 at substantially the same time.

Although not shown in FIGS. 18-22, as with the previously-described embodiment, each microfluidic process channel 24 of the microfluidic chip 18 includes a pair of inlet ports connected to each other by a connector leg formed in the microfluidic chip 18. A secondary flow channel formed in the microfluidic chip 18 extends from the connector leg to the microfluidic process channel 24 of the microfluidic chip 18. As with the previously-described embodiment, a portion of the fluid flowing in primary fluid channel 192 from the sample wells 188 to the vent wells 190 is diverted into the secondary flow fluid channel and is conveyed by the secondary flow channel toward the microfluidic process channel 24. Flows through the secondary flow channel is driven and controlled by selective application of a vacuum at the waste collection wells 208.

Interface cartridge 182 includes a matching alignment hole 215 and slot 213 for positioning the interface cartridge 182 with respect to the microfluidic chip 18. Mounting holes 186 are provided to secure interface cartridge 182 to the microfluidic chip 18.

The pre-interface chip 204 performs master mixing functions for mixing of common reagent and primers. In one exemplary embodiment, a 250 µm diameter by 1 mm deep hole on the bottom of the interface cartridge 182 accepts fluids from the pre-interface chip 204 into the reagent inlet channel 196. A gasket is used to interface between the interface cartridge 182 and the pre-interface chip 204. A bolt 200 and one or more metal plates 216 are used to fasten the pre-interface chip 204 to the interface cartridge 182, and a hole 202 and slot 198 in the interface cartridge 182 are used to align the position of the pre-interface chip 204 to the interface cartridge 182 (see FIG. 22). As one of skill in the art will recognize, these features are only exemplary embodiments of the present invention, and alternative means of construction, attachment, and function may be alternatively utilized.

Exemplary dimensions of the interface cartridge 182 are 54 mm wide×89.5 mm long with a total thickness of 6 mm. Exemplary well diameter is 4.5 mm for greater volume and longer run time (~66 min) as compared to an interface cartridge having smaller diameter wells. One of skill in the art will recognize that such dimensions are only exemplary and alternative dimensions are envisioned and encompassed by the present invention.

Further alterations possible in the interface cartridge 182 may simplify manufacturing. In one embodiment, the interface cartridge 182 comprises only two layers 182a and 182b (see FIGS. 19 and 21). In one embodiment, top layer 182a is 5 mm thick, and bottom layer 182b is 1 mm thick. Moreover, the design has been simplified as compared with other embodiments to reduce manufacturing complexity. In this embodiment, there are no tight tolerance features on the top layer 182a. Further, as shown in FIG. 19, all holes are cut completely through the top layer 182a of the interface cartridge 182, and the wells may be of a size of approximately 79 µL (4.5 mm diameter and 5 mm deep), without a taper on the bottom to allow for more overall well volume. As can be appreciated, other well volumes and sizes are also encompassed by the present invention.

As further shown in FIG. 19, the bottom layer 182b of the interface cartridge 182 can contain all of the critical features of the device, and may be configured to have a bottom layer thickness of 1 mm with reagent delivery channels, primary fluid channels, and fluid removal channels of 300×30 µm dimension and sample delivery channels of 100×30 µm dimension. As can be appreciated, other dimensions are also encompassed by the present invention. Similarly, any dimensions described in the present invention can be understood by one of skill in the art to be exemplary only, such that alternative dimensions are envisioned and are encompassed by the present invention.

In the present embodiment, the interface cartridge bottom layer 182b includes a fluid connection to the pre-interface chip 204, which may be via a hole of approximately 250 µm diameter and 1 mm deep extending through the bottom of the bottom layer 182 from the proximal (left-most) end of reagent inlet channel 196 as discussed above. Fluid delivery ports of similar dimension (250 µm diameter×1 mm deep) may be provided at a delivery interface 218, and fluid removal ports of similar dimension may be provided at waste interface 220.

The present invention contemplates that the bottom layer 182b of the interface cartridge 182 includes the locating holes 212, 202 and slots 214, 198 for the microfluidic chip and pre-interface chip as shown in FIG. 19. Further, as discussed above, the interface cartridge 182 has no tight tolerance features on the top layer 182a. Rather, all locating holes are tight fits on the bottom layer 182b and loose fit on the top 182a.

A further alteration in the interface cartridge 182 as compared to previously-described interface cartridges (such as interface cartridge 102) is that the O-ring grooves and the gasket recesses have been omitted to simplify parts for manufacturing. However, the preferred distance between all channels remains the same as in interface cartridge embodiments discussed previously (i.e., 200 µm).

A rectangular opening 184 is formed through the interface cartridge 182 so as to enable optical detection of properties of fluid flowing through portions of the microfluidic process channels 24 above the opening 184. The delivery interface 218 is formed along one side of the opening 184 and the waste interface 220 is formed along an opposite side of the opening 184.

Figure 22:
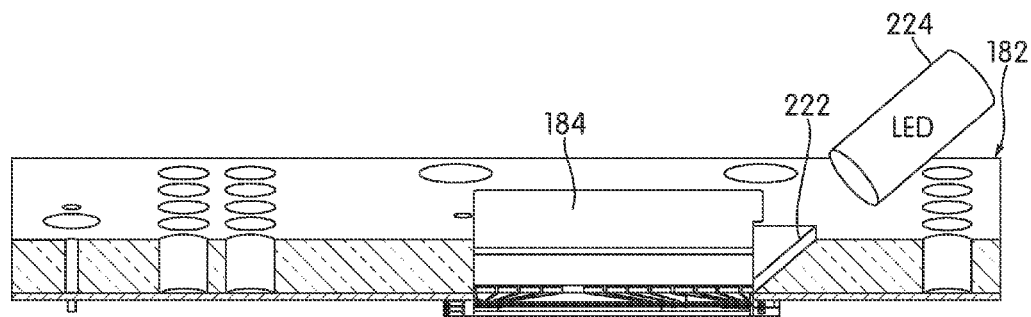
FIG. 22 is a longitudinal cross-section of the interface cartridge shown in FIG. 18 showing an angled slot formed along one edge of a microfluidic chip opening for accommodating an optical detection device.

Further, certain alterations evident in the interface cartridge 182 have been provided for easier assembly. For instance, all channels are at least 600 µm from the edge of a well, reducing the necessary tolerances for aligning the top and bottom of the chip. Furthermore, the line of sight of an optical detector device, such as an LED for detecting an optical property of materials flowing in the microfluidic process channels 24 of the microfluidic chip 18, has been improved by modifications to the interface cartridge 182. First, in accordance with one embodiment as shown in FIG. 22, a 40-degree angled slot 222 (other angles may be used as well) was added to improve the line of sight of the LED 224, and second, as shown in FIG. 18, the waste collection wells 208 were placed further to the right of the opening 184 as compared to embodiments described above. In addition, the fluid delivery channels are positioned such that no channels are under the wells 188, 190, or 208. This allows all the channel intersections to be visible and improves the ability to image the channels via photos and videos during testing.

A further alteration includes a change in the width and length of the sample delivery channels extending from the sample wells 188 to 100 µm×4.5 mm to help improve control flows by increasing the hydraulic resistance in the sample delivery channels. Further, as shown in FIG. 18 and described above, the length of each of the primary fluid channels 192 from the sample well 188 to the microfluidic chip 18 (i.e., the fluid delivery leg of each primary fluid channel 192) is the same for all of the eight channels. Consequently, the fluids will reach the microfluidic chip 18 at the same time for each channel. However, in the embodiment of FIG. 18, the channels back to the vent wells 190 (i.e., the return legs of the primary fluid channels 192) are not the same length. Instead, the channels utilize the straightest route back to the vent wells 190, as do the fluid removal channels 206 from the microfluidic chip 18 to the waste collection wells 208.

Finally, in order to provide flow control feedback, interface cartridge 182 includes redesigned channels such that a section 226 (see FIG. 19) of the interface cartridge has all eight primary fluid channels 192 in a straight, parallel configuration to provide a viewing area for good optical flow control feedback.

Figure 21:
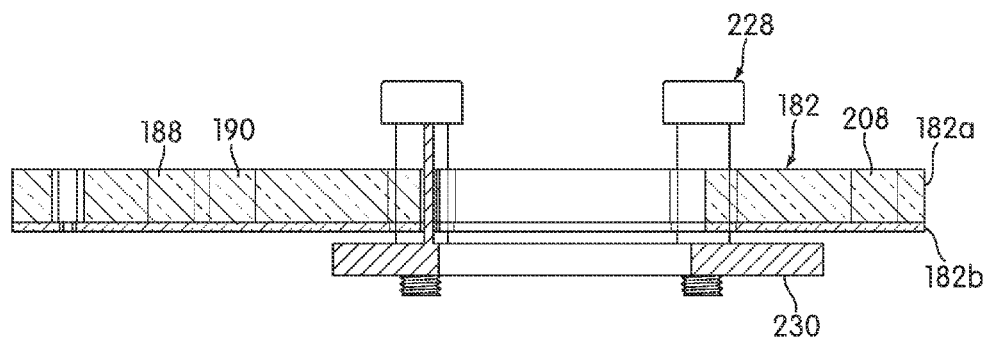
FIG. 21 is a cross-section along the line 21-21 in FIG. 20.

As shown in FIG. 21, in one embodiment, the microfluidic chip 18 is secured to the interface cartridge 182 by means of a chip retainer plate 230 secured with respect to the interface cartridge 182 by means of fasteners 228 (e.g., bolts) extending through mounting holes 186.

Figure 23:
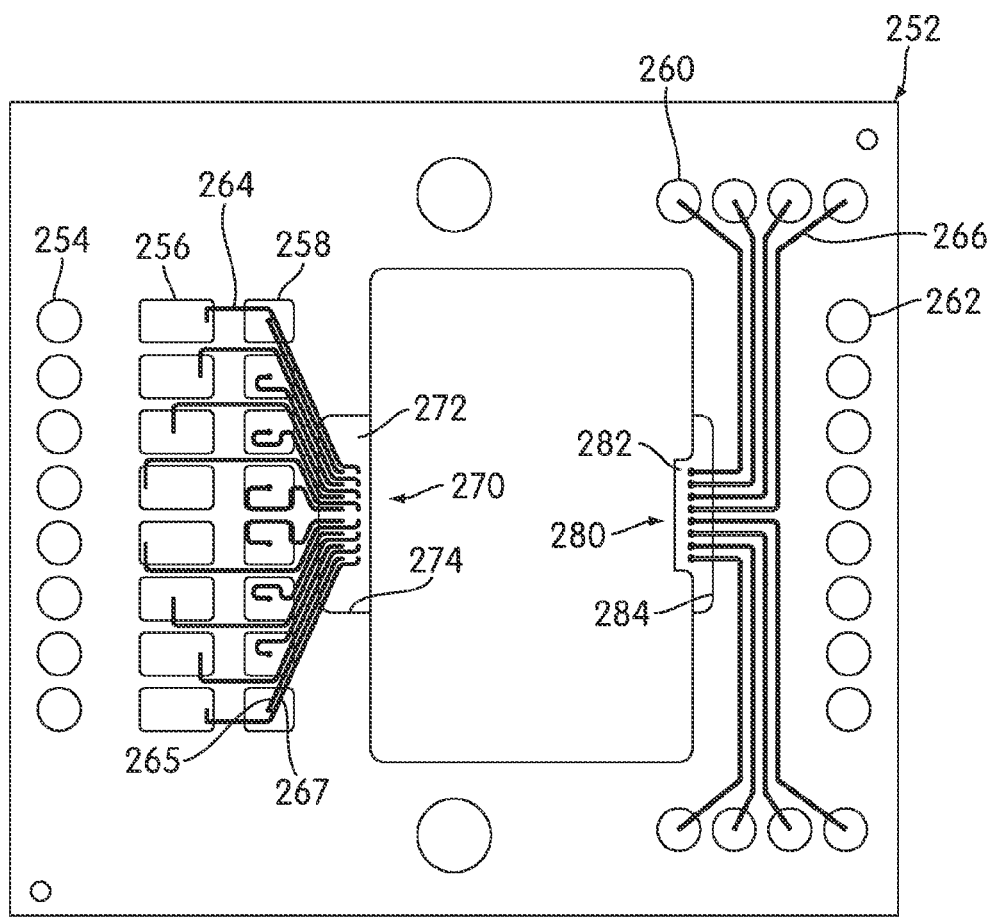
FIG. 23 is a plan view of a further embodiment of an interface cartridge.
Figure 24:
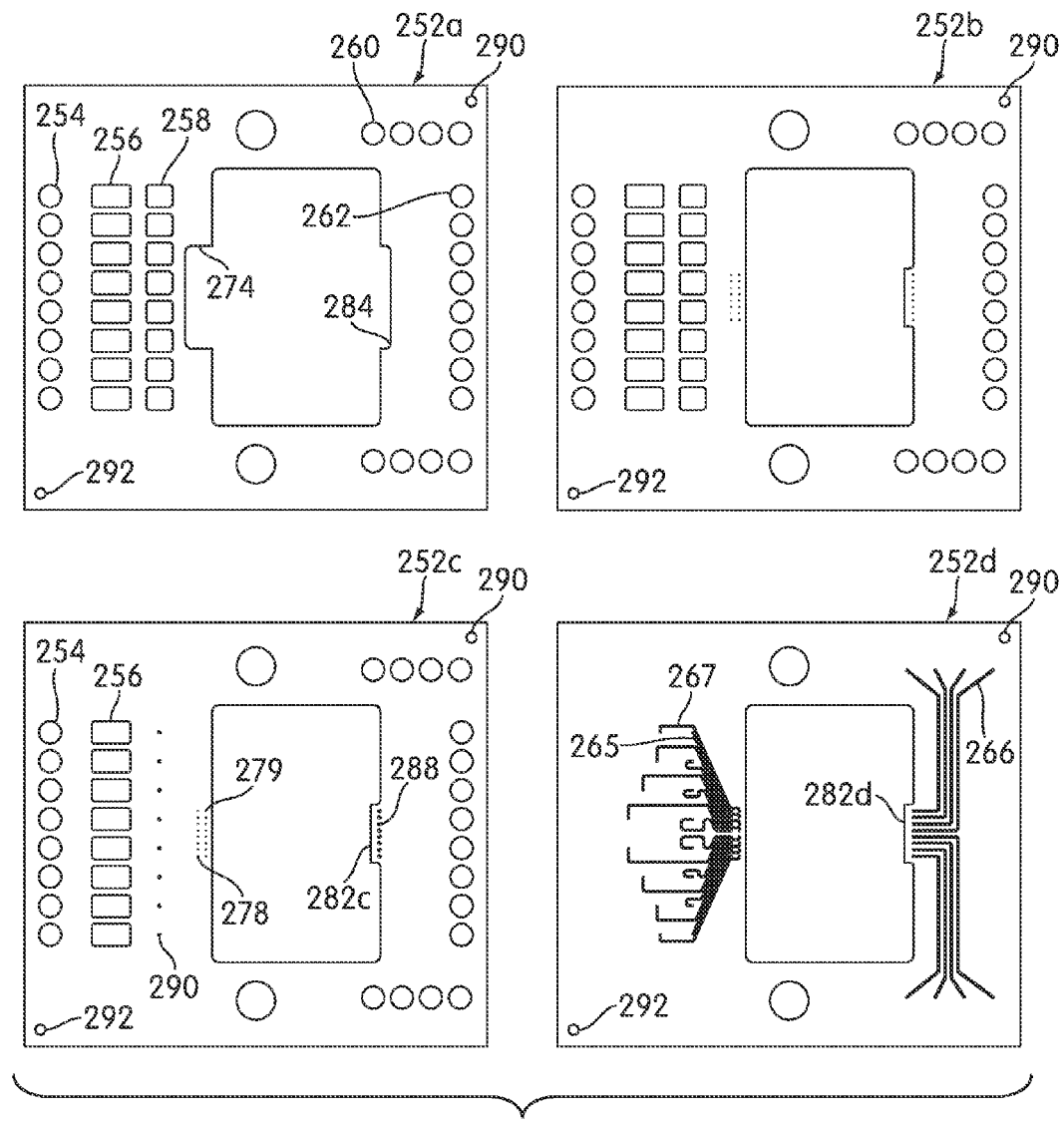
FIG. 24 is a plan view of different layers of the interface cartridge of FIG. 23.
Figure 25:
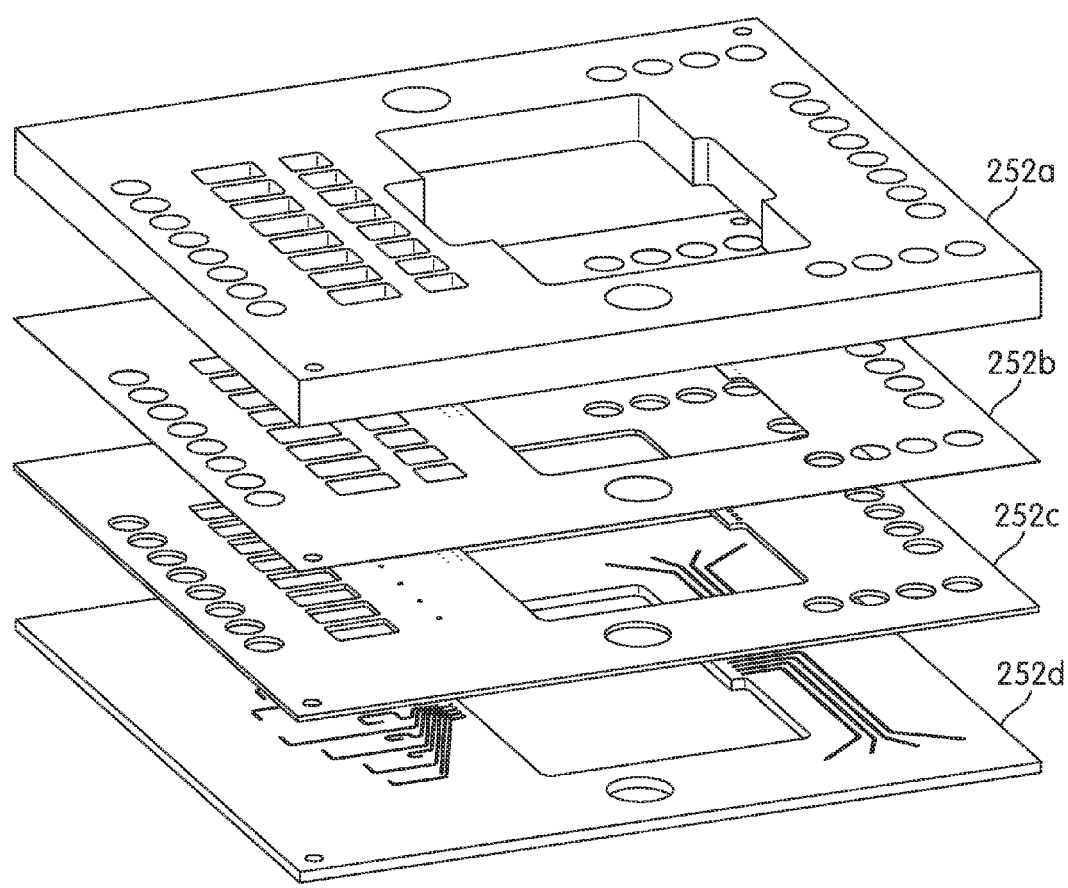
FIG. 25 is an exploded perspective view of the different layers of the embodiment shown in FIG. 23, wherein the layers are stacked one above the other in their assembled order.

Another interface cartridge embodying aspects of the present invention is indicated by reference number 252 in FIGS. 23-25. A first row of wells formed in the top side of the interface cartridge 252 comprises patient sample wells 254 in which a user would add the samples to be tested. Alternatively, patient sample well may be external to the interface cartridge 252. A row of vent wells 256 is provided to collect excess sample and reagent fluids. A row of input wells 258 is provided to receive sample and/or reagent fluids, which may be pre-mixed, and are dispensed by means of, for example, a pipette or other suitable device. Sample fluid may be transferred from one of the patient sample wells 254 to an input well 258 by means of, for example, a pipetter. Waste collection wells 260 are provided to collect the remains of the assay mixture removed from the microfluidic process channels of the microfluidic chip. A row of spacer fluid wells 262 is provided to hold spacer fluids to be delivered to the microfluidic process channels between fluid samples to form discrete sample segments within a fluid flow through the microfluidic process channels. Sample fluid may be transferred from one of the spacer fluid wells 262 to an input well 258 by means of, for example, a pipetter. Alternatively, the spacer fluid wells may be external to the interface cartridge 252.

Interface cartridge 252 includes fluid delivery channels configured to convey fluids (sample, reagents, etc.) from the wells 258 to the microfluidic process channels 24 of the microfluidic chip 18. More specifically, the fluid delivery channels include primary fluid channels 264 connecting each input well 258 with one vent well 256. In the illustrated embodiment, interface cartridge 252 includes eight primary channels 264, corresponding to eight associated input wells 258 and vent wells 256. Fluid removal channels 266 connect each waste collection well 260 to an associated one of the microfluidic process channels 24.

The inlet ports of microfluidic process channels of a microfluidic chip are fluidly coupled to the fluid delivery channels of the interface cartridge 252 at a delivery interface 270. The outlet ports of the microfluidic process channels are fluidly coupled to the fluid removal channels 266 at a waste interface 280 at which a fluid removal port, which comprises the terminal end of each fluid removal channel 280, is coupled in fluid-communication with the outlet port of an associated microfluidic process channel of the microfluidic chip.

Each primary fluid channel 264 comprises a delivery leg 265 conveying a fluid (e.g., a mixture of sample and reagent) from the input well 258 toward the delivery interface 270 coupling the interface cartridge 252 with a microfluidic chip and a return leg 267 conveying excess fluid mixture (i.e., that portion of the fluid mixture that is not drawn into the associated microfluidic process channels 24) back to the vent well 256. Flow through the primary fluid channels 264 from the input wells 258 to the vent wells 256 may be driven and controlled by selective application of a vacuum at the vent wells 256.

Note that, as with previously-described embodiments, delivery legs 265 of the primary fluid channels 264 progressing from the lateral perimeter of the cartridge body toward the center of the cartridge body includes an increasingly large deviation from a direct, straight-line path. This results in each of the delivery legs of the primary fluid channels 264 having a substantially identical length, so that fluid flowing from the wells 258 through the delivery legs will arrive at the microfluidic chip 18 at substantially the same time.

Although not shown in FIGS. 23-25, as with the previously-described embodiment, each microfluidic process channel of the microfluidic chip includes a pair of inlet ports connected to each other by a connector leg formed in the microfluidic chip. A secondary flow channel formed in the microfluidic chip extends from the connector leg to the microfluidic process channel of the microfluidic chip. As with previously-described embodiments, a portion of the fluid flowing in primary fluid channel 264 from the input wells 258 to the vent wells 256 is diverted into the secondary flow fluid channel and is conveyed by the secondary flow channel toward the microfluidic process channel. Flows through the secondary flow channel is driven and controlled by selective application of a vacuum at the waste collection wells 260.

As shown in FIG. 24, the interface cartridge 252 may be made from multiple layers. For example, in the illustrated embodiment, the cartridge has four layers. The top layer 252a is a 5 mm (note that dimensions are exemplary) thick layer made from polymethyl methacrylate (PMMA), or some other suitable material, including non-reactive plastics or acrylic. Various features of the interface cartridge 252 are formed in the top layer 252a, including sample wells 254, vent wells 256, input wells 258, waste collection wells 260, and spacer fluid wells 262. The top layer further includes cut-outs 274, 284 for receiving the ends of the microfluidic chip. Layer 252b is a pressure sensitive adhesive ("PSA") layer generally conforming to the shape of top layer 252a. Middle layer 252c is a 0.7 mm thick layer formed from PMMA, or other suitable material (all layers, except the PSA layer, are preferably formed from the same material). Layer 252c includes sample wells 254, vent wells 256, waste collection wells 260, and spacer fluid wells 262, but lacks input wells 258. Instead, layer 252c includes a row of fluid connection holes 290 formed through the layer which communicate with input wells 258 formed in layer 252a. Layer 252c also includes a row of fluid removal ports 288 and two rows of fluid holes 278 and 279. Bottom layer 252d is a 0.7 mm thick layer formed from PMMA, or other suitable material. Layer 252d includes all the fluid delivery channels, including fluid delivery legs 265 and fluid return legs 267 of the primary fluid channels 264 and the fluid removal channels 266.

The layers 252a, 252b, 252c, 252d are assembled as shown in FIG. 25. In one embodiment, bottom layer 252d is thermally bonded to middle layer 252c, and the top layer 252a is secured to middle layer 252c by PSA layer 252b between the top layer 252a and the middle layer 252c.

When the layers 252a-d are assembled, the terminal end of each of the fluid delivery legs 265 formed in layer 252d is aligned with one of the fluid holes 278 formed in layer 252c, and the terminal end of each fluid return leg 267 formed in layer 252d is aligned with one of the fluid holes 279 formed in layer 252c.

Similarly, the terminal end of each fluid removal channel 266 is aligned with one of the fluid removal ports 288 formed through layer 252c. The proximal ends of the delivery legs 265 align with holes 290 so as to be in fluid-communication with input wells 258, and the proximal ends of the return legs 267 align with vent wells 256. The proximal ends of the fluid removal channels 266 align with the waste collection wells 260.

The end of a microfluidic chip (not shown) with a pair of inlet ports for each microfluidic process channel is placed within the cutout 274 associated with the delivery interface 270. A portion of middle layer 252c beneath the cutout 274 forms a support shelf 272 that supports the end of the microfluidic chip. The inlet ports of the microfluidic chip are configured so as to be in alignment with the holes 278, 279 when the chip is placed on support shelf 272 within cutout 274. The opposite end of the microfluidic chip is placed within cutout 284 associated with waste interface 280 and is supported on a portion of the middle layer 252c beneath the cutout 284 defining a support shelf 282. The outlet ports of the microfluidic chip are configured so as to be in alignment with holes 288 formed in middle layer 252c chip is placed on support shelf 282 within cutout 284.

While the present invention has been described and shown in considerable detail with disclosure to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A microfluidic assembly comprising:
   a microfluidic assay chip comprising:
      a plurality of microfluidic channels;
      two inlet ports associated with each of said microfluidic channels, wherein each pair of inlet ports associated with each microfluidic channel are connected by an interconnecting channel that is in fluid-communication with a proximal end of the associated microfluidic channel; and
      an outlet port for removing fluid from a terminal end of the microfluidic channel; and
   an interface cartridge comprising:
      a plurality of fluid delivery channels in fluid-communication with the interconnecting channel of each of one or more microfluidic channels in the microfluidic assay chip; and
      a delivery interface configured to fluidly couple said fluid delivery channels of said interface cartridge to the microfluidic assay chip, said delivery interface including a plurality of fluid delivery ports, wherein each fluid delivery port is associated with one fluid delivery channel and is configured to deliver fluid from the fluid delivery channel to an interconnecting channel of the one or more microfluidic channels.

2. The microfluidic assembly of claim 1, wherein each fluid delivery channel of the interface cartridge comprises:
   a first leg and a second leg, each leg having a proximal end and a terminal end; and
   a vent well at the terminal end of said second leg of said fluid delivery channel;
   wherein one of said inlet ports of said microfluidic assay chip is in fluid-communication with the terminal end of said first leg of said fluid delivery channel and the other of said inlet ports is in fluid-communication with the proximal end of said second leg of said fluid delivery channel.

3. The microfluidic assembly of claim 2, further comprising a fluid inlet well at the proximal end of the first leg of each fluid delivery channel.

4. The microfluidic assembly of claim 1, wherein said interface cartridge further includes a plurality of fluid removal channels corresponding in number to the number of microfluidic channels in the microfluidic assay chip and a waste interface configured to fluidly couple said fluid removal channels of said interface cartridge to said microfluidic assay chip, said waste interface including a plurality of fluid transfer ports corresponding in number to the number of microfluidic channels in the microfluidic assay chip, wherein each fluid transfer port is associated with one fluid removal channel and is configured to receive fluid from an associated outlet port of one of the microfluidic channels.

5. The microfluidic assembly of claim 4, wherein said interface cartridge further comprises a waste collection well disposed at a terminal end of each fluid removal channel.

6. The microfluidic assembly of claim 1, wherein the path of the first leg of each fluid delivery channel is configured so that the lengths of the first legs of all fluid delivery channels are the same.

7. The microfluidic assembly of claim 4, wherein the path of each fluid removal channel is configured so that the lengths of all fluid removal channels are the same.

8. The microfluidic assembly of claim 1, wherein said plurality of fluid delivery channels corresponds in number to the number of microfluidic channels in the microfluidic assay chip.

9. The microfluidic assembly of claim 1, wherein said interface cartridge further comprises a sample port associated with each fluid delivery channel, each sample port being in fluid-communication with its associated fluid delivery channel and being configured for introducing a sample fluid into the associated fluid delivery channel.

10. The microfluidic assembly of claim 1, wherein said interface cartridge further comprises a common reagent port in fluid-communication with all the fluid delivery channels and configured to introduce a reagent fluid into all the fluid delivery channels.

11. The microfluidic assembly of claim 1, further comprising a sipper tube extending from said interface cartridge so that a distal end thereof can be placed into a reagent reservoir so that reagent can be drawn from the reservoir and into said sipper, wherein said sipper is in fluid-communication with all said fluid delivery channels so that a reagent fluid drawn into said sipper can be introduced into all said fluid delivery channels.

12. The microfluidic assembly of claim 1, wherein said interface cartridge further comprises:
a sample port associated with each fluid delivery channel, each sample port being in fluid-communication with its associated fluid delivery channel and being configured for introducing a sample fluid into the associated fluid delivery channel; and
a common reagent port in fluid-communication with all the fluid delivery channels and configured to introduce a reagent fluid into all the fluid delivery channels;
and wherein said microfluidic assembly further comprises a sipper tube extending from said interface cartridge so that a distal end thereof can be placed into a reagent reservoir so that reagent can be drawn from the reservoir and into said sipper, wherein said sipper is in fluid-communication with all said fluid delivery channels so that a reagent fluid drawn into said sipper can be introduced into all said fluid delivery channels.

13. The microfluidic assembly of claim 1, wherein said interface cartridge is made from a polymer.

14. The microfluidic assembly of claim 13, wherein said polymer comprises a transparent polymer.

15. The microfluidic assembly of claim 14, wherein said interface cartridge is made from polymethyl methacrylate (PMMA).

16. The microfluidic assembly of claim 14, wherein said microfluidic assay chip is made from glass or silica quartz.

17. The microfluidic assembly of claim 1, wherein said interface cartridge is made from two or more layers.

18. The microfluidic assembly of claim 1, further comprising a gasket at the delivery interface disposed between said interface cartridge and said microfluidic assay chip.

19. The microfluidic assembly of claim 4, further comprising a gasket at the waste interface disposed between said interface cartridge and said microfluidic assay chip.

20. The microfluidic assembly of claim 1, wherein said interface cartridge further comprises:
a sample input well disposed at a proximal end of each of said fluid delivery channels; and
a plurality of reagent input wells, each of said reagent input wells being in fluid-communication with each of said fluid delivery channels.

21. The microfluidic assembly of claim 20, wherein said interface cartridge further comprises a plurality of h-channels fluidly connecting each of said reagent input wells to each of the fluid delivery channels.

22. The microfluidic assembly of claim 20, wherein said interface cartridge comprises eight sample input wells, eight vent wells, and eighty reagent input wells.

23. The microfluidic assembly of claim 22, wherein said interface cartridge comprises eight fluid delivery channels and further comprises a plurality of h-channels fluidly connecting each of said reagent input wells to each of the fluid delivery channels.

24. The microfluidic assembly of claim 4, wherein said interface cartridge has a rectangular shape and comprises a rectangular opening formed therein and wherein said delivery interface is disposed on one side of said rectangular opening and said waste interface is disposed on an opposite side of said rectangular opening.

25. The microfluidic assembly of claim 24, wherein said interface cartridge further comprises an angled slot formed along one edge of said rectangular opening.

26. The microfluidic assembly of claim 11, wherein said fluid delivery channel further comprises a sample flow region, a reagent flow region and a mixing region configured to permit mixing of said sample and said reagent, said mixing region being located at an intersection of said sample flow region and said reagent flow region.

27. The microfluidic assembly of claim 26, wherein said mixing region is located upstream from said interconnecting channel.

28. The microfluidic assembly of claim 3, wherein said fluid inlet well is adapted to receive a premixed solution of sample and one or more reagents.

* * * * *